US010278840B2

(12) United States Patent
Tippett et al.

(10) Patent No.: US 10,278,840 B2
(45) Date of Patent: May 7, 2019

(54) ENDOVASCULAR PROSTHESIS AND METHOD FOR DELIVERY OF AN ENDOVASCULAR PROSTHESIS

(71) Applicant: EVYSIO MEDICAL DEVICES ULC, Vancouver (CA)

(72) Inventors: Jonathan G. Tippett, Vancouver (CA); Eric Soun-Sang Fung, Vancouver (CA); Donald R. Ricci, Vancouver (CA); Ian M. Penn, Vancouver (CA)

(73) Assignee: Evasc Neurovascular Limited Partnership, Vancouver (CA)

( * ) Notice: Subject to any disclaimer, the term of this patent is extended or adjusted under 35 U.S.C. 154(b) by 396 days.

(21) Appl. No.: 14/439,033

(22) PCT Filed: Oct. 31, 2013

(86) PCT No.: PCT/CA2013/000921
§ 371 (c)(1),
(2) Date: Apr. 28, 2015

(87) PCT Pub. No.: WO2014/066982
PCT Pub. Date: May 8, 2014

(65) Prior Publication Data
US 2015/0313737 A1    Nov. 5, 2015

Related U.S. Application Data

(60) Provisional application No. 61/795,958, filed on Oct. 31, 2012.

(51) Int. Cl.
*A61F 2/86*     (2013.01)
*A61F 2/954*    (2013.01)
(Continued)

(52) U.S. Cl.
CPC .......... *A61F 2/86* (2013.01); *A61B 17/12113* (2013.01); *A61B 17/12172* (2013.01);
(Continued)

(58) Field of Classification Search
CPC .. A61F 2/844; A61F 2/91; A61F 2/915; A61F 2/92; A61F 2002/825;
(Continued)

(56) References Cited

U.S. PATENT DOCUMENTS 5,954,765 A * 9/1999 Ruiz .................... A61F 2/92
                                                  606/194
7,815,674 B1 * 10/2010 Ragazzo ................ A61F 2/844
                                                  623/1.23
(Continued)

FOREIGN PATENT DOCUMENTS

JP    2004-522493 A    7/2004
RU    2089132 C1       9/1997
(Continued)

OTHER PUBLICATIONS

Examination Report No. 1 for Australian Patent Application No. 2013337549 dated Oct. 27, 2017.
(Continued)

*Primary Examiner* — Robert A Lynch
(74) *Attorney, Agent, or Firm* — Katten Muchin Rosenman LLP

(57) ABSTRACT

There is disclosed a novel endovascular prosthesis that has an improved rotational range of proper placement of the prosthesis with respect to the opening of the aneurysm and provides improved flexibility with respect to longitudinal positioning of the device in the artery. This provides the clinician with a significant advantage over the prior art devices described above. The present elongate endovascular prosthesis comprises a first expandable portion expandable
(Continued)

from a first, unexpanded state to a second, expanded state to urge the first expandable portion against the wall of the vascular lumen such as an artery. The endovascular prosthesis further comprises a retractable leaf portion attached to the first expandable portion; the retractable leaf portion serves to facilitate stasis and thrombotic occlusion of the aneurysm. The retractable leaf portion comprises at least one spine portion and a plurality of rib portions attached to the spine portion.

34 Claims, 16 Drawing Sheets

(51) Int. Cl.
*A61F 2/844* (2013.01)
*A61B 17/12* (2006.01)
*A61F 2/82* (2013.01)
*A61B 17/00* (2006.01)
*A61B 90/00* (2016.01)

(52) U.S. Cl.
CPC .............. *A61F 2/844* (2013.01); *A61F 2/954* (2013.01); *A61B 2017/00526* (2013.01); *A61B 2017/00867* (2013.01); *A61B 2017/00871* (2013.01); *A61B 2017/1205* (2013.01); *A61B 2090/3966* (2016.02); *A61F 2002/823* (2013.01); *A61F 2002/825* (2013.01)

(58) Field of Classification Search
CPC .. A61F 2002/91508; A61F 2002/91516; A61F 2002/91525; A61F 2002/91533; A61F 2002/91558
See application file for complete search history.

(56) References Cited

U.S. PATENT DOCUMENTS

| 7,942,917 | B2* | 5/2011 | Nowak, Jr. ............... A61F 2/88 |
| | | | 623/1.11 |
| 8,187,315 | B1 | 5/2012 | Clauson et al. |
| 8,979,919 | B2 | 3/2015 | Goddard et al. |
| 2002/0052648 | A1* | 5/2002 | McGuckin, Jr. .......... A61F 2/07 |
| | | | 623/1.35 |
| 2002/0173839 | A1 | 11/2002 | Leopold et al. |
| 2004/0149294 | A1* | 8/2004 | Gianchandani .......... B23H 9/00 |
| | | | 128/879 |
| 2008/0046069 | A1 | 2/2008 | Keeble et al. |
| 2009/0171439 | A1 | 7/2009 | Nissl |

FOREIGN PATENT DOCUMENTS

| WO | 00/47134 A1 | 8/2000 |
| WO | 2007/117645 A2 | 10/2007 |
| WO | 2012/145823 A1 | 11/2012 |

OTHER PUBLICATIONS

Office Action for Japanese Patent Application No. 2015-540003 dated Aug. 8, 2017.
Office Action for Japanese Patent Application No. 2015-540003 dated Jan. 23, 2018.
Dec. 21, 2017 letter from Oliveres to Gowlings summarizing and Office Action for Mexican Patent Application No. MX/a/2015/005591.
May 7, 2018 Office Action for Mexican Patent Application No. MX/a/2015/005591, and a letter from Oliveres to Gowlings summarizing the Office Action in English.
Office Action for Russian Patent Application No. 2015116319 dated Nov. 14, 2017.

* cited by examiner

ENDOVASCULAR PROSTHESIS AND METHOD FOR DELIVERY OF AN ENDOVASCULAR PROSTHESIS

CROSS-REFERENCE TO RELATED APPLICATION

None.

BACKGROUND OF THE INVENTION

Field of the Invention

In one of its aspects, the present invention relates to an endovascular prosthesis. In another of its aspects, the present invention relates to a method of treating an aneurysm in a patient. In another of its aspects, the present invention relates to a method for delivering an endovascular prosthesis. Other aspects of the invention will be apparent to those of skill in the art having in hand the present specification.

Description of the Prior Art

As is known in the art, an aneurysm is an abnormal bulging outward in the wall of an artery. In some cases, the bulging may be in the form of a smooth bulge outward in all directions from the artery—this is known as a "fusiform aneurysm". In other cases, the bulging may be in the form of a sac arising from an arterial branching point or from one side of the artery—this is known as a "saccular aneurysm".

While aneurysms can occur in any artery of the body, it is usually those which occur in the brain which lead to the occurrence of a stroke. Most saccular aneurysms which occur in the brain have a neck which extends from the cerebral blood vessel and broadens into a pouch which projects away from the vessel.

The problems caused by such aneurysms can occur in several different ways. For example, if the aneurysm ruptures, blood enters the brain or the subarachnoid space (i.e., the space closely surrounding the brain)—the latter is known as an aneurysmal subarachnoid hemorrhage. This is followed by one or more of the following symptoms: nausea, vomiting, double vision, neck stiffness and loss of consciousness. Aneurysmal subarachnoid hemorrhage is an emergency medical condition requiring immediate treatment. Indeed, 10-15% of patients with the condition die before reaching the hospital for treatment. More than 50% of patients with the condition will die within the first thirty days after the hemorrhage. Of those patients who survive, approximately half will suffer a permanent stroke. Some of these strokes occur one to two weeks after the hemorrhage itself from vasospasm in cerebral vessels induced by the subarachnoid hemorrhage. Aneurysms also can cause problems which are not related to bleeding although this is less common. For example, an aneurysm can form a blood clot within itself which can break away from the aneurysm and be carried downstream where it has the potential to obstruct an arterial branch causing a stroke (e.g., an ischemic stroke). Further, the aneurysm can also press against nerves (this has the potential of resulting in paralysis or abnormal sensation of one eye or of the face) or the adjacent brain (this has the potential of resulting in seizures).

Given the potentially fatal consequences of the aneurysms, particularly brain aneurysms, the art has addressed treatment of aneurysms using various approaches.

Generally, aneurysms may be treated from outside the blood vessels using surgical techniques or from the inside using endovascular techniques (the latter falls under the broad heading of interventional (i.e., non-surgical techniques).

Surgical techniques usually involve a craniotomy requiring creation of an opening in the skull of the patient through which the surgeon can insert instruments to operate directly on the brain. In one approach, the brain is retracted to expose the vessels from which the aneurysm arises and then the surgeon places a clip across the neck of the aneurysm thereby preventing arterial blood from entering the aneurysm. If there is a clot in the aneurysm, the clip also prevents the clot from entering the artery and obviates the occurrence of a stroke. Upon correct placement of the clip the aneurysm will be obliterated in a matter of minutes. Surgical techniques are the most common treatment for aneurysms. Unfortunately, surgical techniques for treating these conditions are regarded as major surgery involving high risk to the patient and necessitate that the patient have strength even to have a chance to survive the procedure.

As discussed above, endovascular techniques are non-surgical techniques and are typically performed in an angiography suite using a catheter delivery system. Specifically, known endovascular techniques involve using the catheter delivery system to pack the aneurysm with a material which prevents arterial blood from entering the aneurysm—this technique is broadly known as embolization. One example of such an approach is the Guglielmi Detachable Coil which involves intra-aneurysmal occlusion of the aneurysm via a system which utilizes a platinum coil attached to a stainless steel delivery wire and electrolytic detachment. Thus, once the platinum coil has been placed in the aneurysm, it is detached from the stainless steel delivery wire by electrolytic dissolution. Specifically, the patient's blood and the saline infusate act as the conductive solutions. The anode is the stainless steel delivery wire and the cathode is the ground needle which is placed in the patient's groin. Once current is transmitted through the stainless steel delivery wire, electrolytic dissolution will occur in the uninsulated section of the stainless steel detachment zone just proximal to the platinum coil (the platinum coil is of course unaffected by electrolysis). Other approaches involve the use of materials such as cellulose acetate polymer to fill the aneurysm sac. While these endovascular approaches are an advance in the art, they are disadvantageous. Specifically, the risks of these endovascular approaches include rupturing the aneurysm during the procedure or causing a stroke (e.g., an ischemic stroke) due to distal embolization of the device or clot from the aneurysm. Additionally, concern exists regarding the long term results of endovascular aneurysm obliteration using these techniques. Specifically, there is evidence of intra-aneurysmal rearrangement of the packing material and reappearance of the aneurysm on follow-up angiography.

One particular type of brain aneurysm which has proven to be very difficult to treat, particularly using the surgical clipping or endovascular embolization techniques discussed above occurs at the distal basilar artery. This type of aneurysm is a weak outpouching, usually located at the terminal bifurcation of the basilar artery. Successful treatment of this type of aneurysm is very difficult due, at least in part, to the imperative requirement that all the brainstem perforating vessels be spared during surgical clip placement.

Unfortunately, there are occasions when the size, shape and/or location of an aneurysm make both surgical clipping and endovascular embolization not possible for a particular patient. Generally, the prognosis for such patients is not good.

Accordingly, while the prior art has made advances in the area of treatment of aneurysms, there is still room for improvement, particularly in endovascular embolization since it is such an attractive alternative to major surgery.

In International Publication Number WO 99/40873 [Marotta et al. (Marotta)], published Aug. 19, 1999, there is taught a novel endovascular approach useful in blocking of an aneurysmal opening, particularly those in saccular aneurysms, leading to obliteration of the aneurysm. The approach is truly endovascular in that, with the endovascular prosthesis taught by Marotta, there is no requirement to pack the aneurysmal sac with a material (e.g., such is used with the Guglielmi Detachable Coil). Rather, the endovascular prosthesis taught by Marotta operates on the basis that it serves to block the opening to the aneurysmal sac thereby obviating the need for packing material. Thus, the endovascular prosthesis taught by Marotta is an important advance in the art since it obviates or mitigates many of the disadvantages of the prior art. The endovascular prosthesis taught by Marotta comprises a leaf portion capable of being urged against the opening of the aneurysm thereby closing the aneurysm. In the endovascular prosthesis taught by Marotta, the leaf portion is attached to, and independently moveable with respect to, a body comprising at least one expandable portion. The expandable portion is expandable from a first, unexpanded state to a second, expanded state with a radially outward force thereon. Thus, the body serves the general purpose of fixing the endovascular prosthesis in place at a target body passageway or vascular lumen in the vicinity at which the aneurysmal opening is located and the leaf portion serves the purpose of sealing the aneurysmal opening thereby leading to obliteration of the aneurysm. Thus, as taught by Marotta, the leaf portion functions and moves independently of the body of the endovascular prosthesis.

U.S. provisional patent application Ser. Nos. 61/457,604 and 61/457,605 [both in the name of Tippett et al. (Tippett)] teaches an endovascular prosthesis comprising a first expandable portion expandable from a first, unexpanded state to a second, expanded state to urge the first expandable portion against a vascular lumen and a retractable leaf portion attached to the first expandable portion. The retractable leaf portion comprises at least one spine portion and a plurality of rib portions attached to the spine portion. Longitudinally adjacent pairs of rib portions are free of interconnecting struts. The endovascular prosthesis can be unsheathed and re-sheathed for repositioning of the endovascular prosthesis prior to final deployment thereof. There is also described a delivery device that that is particularly well suited to delivering the present endovascular prosthesis through tortuous vasculature in the body.

While the endovascular prosthesis taught by Tippett is a significant advance in the art, there is still room for improvement. Specifically, in the preferred embodiment of the endovascular prosthesis taught by Tippett, relatively precise placement of the prosthesis across the opening of the aneurysm is required. Put another way, the rotational range of proper placement of the prosthesis with respect to the opening of the aneurysm is relatively limited. This, coupled with variability in human vasculature and in the size/orientation of the aneurysm can present additional challenges to correct implantation of the prosthesis in the patient. While this may not be a problem in all instances, as a general matter, the physician would welcome a prosthesis of this type having an improved rotational range of proper placement of the prosthesis with respect to the opening of the aneurysm.

Accordingly, there remains a need in the art for an endovascular prosthesis that may be retrieved by the physician after it has been partially or fully deployed (in the case of a self expanding endovascular prosthesis) and that has an improved rotational range of proper placement of the prosthesis with respect to the opening of the aneurysm.

SUMMARY OF THE INVENTION

It is an object of the present invention to obviate or mitigate at least one of the above-mentioned disadvantages of the prior art.

It is another object of the present invention to provide a novel endovascular prosthesis.

Accordingly, in one of its aspects, the present invention provides an endovascular prosthesis comprising:

a first expandable portion expandable from a first, unexpanded state to a second, expanded state to urge the first expandable portion against a vascular lumen; and a retractable leaf portion attached to the first expandable portion, the retractable leaf portion comprising at least one spine portion and a plurality of rib portions attached to the spine portion, the retractable leaf portion configured such that a pair of ribs attached on opposite sides of a longitudinally straightened configuration of the spine portion in a plane of view normal to a central axis of the prosthesis defines a shape, in two dimensions, that is substantially non-circular.

In another of its aspects, the present invention provides an endovascular prosthesis comprising:

a first expandable portion expandable from a first, unexpanded state to a second, expanded state to urge the first expandable portion against a vascular lumen; and a retractable leaf portion attached to the first expandable portion, the retractable leaf portion comprising at least one spine portion and a plurality of rib portions attached to the spine portion, the retractable leaf portion configured such that a pair of ribs attached on opposite sides of a longitudinally straightened configuration of the spine portion in a plane of view normal to a central axis of the prosthesis defines a shape, in two dimensions, through which one straight line can be translated from one side to the other side of the shape so as to traverse the shape only once at every point along the shape.

In yet a further aspect, the present invention provides A method for delivering the endovascular prosthesis to a bifurcated artery having a main passageway, a first passageway and a second passageway, the method comprising the steps of:

(a) placing a guidewire and delivery catheter in first passageway such that the guidewire emanates from the delivery catheter;

(b) passing a combination of the endovascular prosthesis interconnected to a delivery device through the delivery catheter such that a first end of the endovascular prosthesis is urged against a portion of the first passageway;

(c) withdrawing the guidewire from the first passageway;

(d) placing the guidewire in the second passageway;

(e) passing the combination over the guidewire such that a second end of the endovascular prosthesis is urged against a portion of the second passageway;

(f) detaching the delivery device from the endovascular prosthesis; and (g) withdrawing the delivery device and the guidewire.

Thus, the present inventors have discovered a novel endovascular prosthesis that has an improved rotational range of proper placement of the prosthesis with respect to the opening of the aneurysm and provides improved flexibility with respect to longitudinal positioning of the device in the artery. This provides the clinician with a significant advantage over the prior art devices described above. The present elongate endovascular prosthesis comprises a first expandable portion expandable from a first, unexpanded state to a second, expanded state to urge the first expandable portion against the wall of the vascular lumen such as an artery. The endovascular prosthesis further comprises a retractable leaf portion attached to the first expandable portion; the retractable leaf portion serves to facilitate stasis and thrombotic occlusion of the aneurysm. The retractable leaf portion comprises at least one spine portion and a plurality of rib portions attached to the spine portion. Importantly, in one preferred embodiment of the present endovascular prosthesis, the retractable leaf portion is configured such that a pair of ribs attached on opposite sides of a longitudinally straightened configuration of the spine portion in a plane of view normal to a central axis of the prosthesis defines a shape, in two dimensions, that is substantially non-circular. In another preferred embodiment of the present endovascular prosthesis, the retractable leaf portion is configured such that a pair of ribs attached on opposite sides of a longitudinally straightened configuration of the spine portion in a plane of view normal to a central axis of the prosthesis defines a shape, in two dimensions, through which one straight line can be translated from one side to the other side of the shape so as to traverse the shape only once at every point along the shape.

A particular advantage of the present endovascular prosthesis is that it allows for simplified delivery. Specifically, the prosthesis may be deployed by using a single guidewire to deliver the expandable portion of the prosthesis in one of the pair of secondary passageways of a bifurcated artery and the leaf portion across the opening of the aneurysm and most cases in the other of the pair of secondary passageways. In broader sense, the simplified delivery method may be used to deliver any endovascular prosthesis to a bifurcated artery such that each opposed end of the endovascular prosthesis is delivered to each of the pair of secondary passageways in a bifurcated artery using a single guidewire and a single delivery system.

In addition, the present endovascular prosthesis is advantageous in that it has a natural tendency to flex in a manner such that the spine portion is on the outside of the bend. This is highly advantageous, especially when the device is implanted in a bifurcated body passageway. An additional advantage is that the orientation of the rib portions, coupled with the flex, particularly facilitates atraumatic and accurate delivery and deployment of the present endovascular prosthesis.

While not wishing to be bound by any particular theory or mode of action, it has been found that the rib portions of the present endovascular prosthesis can be designed so as to provide an improved rotational range of proper placement of the prosthesis with respect to the opening of the aneurysm. In a preferred embodiment, the rotational range may be as much as 45° or more (as will be described in more detail below).

In a highly advantageous embodiment, the present endovascular prosthesis is configured to be self-expanding. This means that the device may be sheathed or otherwise restrained prior to deployment and after initial delivery of the device, the sheath or restraint is partially retracted thereby allowing the device to self-expand. This allows for partial and progressive deployment of the device. The self-expanding aspect of the device combined the prosthesis's shape or architecture has the additional advantage that the clinician can re-sheath the device if initial partial or full deployment of the endovascular prosthesis is not in the correct position with respect to the target anatomy of the patient. In this context, it is also possible to deploy the prosthesis fully or partially and if axial or rotational orientation is incorrect, achieve an additional rotational orientation of the present endovascular prosthesis by resheathing the prosthesis and re-orientating the prosthesis. Delivering, rotationally orientating, unsheathing and resheathing of the prosthesis is achieved using a 'torquable catheter'. Positioning of the prosthesis usually involves partially deploying the prosthesis to evaluate rotational orientation. If the rotation of the device relative to the aneurysm neck needs to be adjusted, the prosthesis may be retracted into the torquable catheter, torqued into another orientation and then these steps are repeated until the prosthesis is deemed to be in the correct position relative to the aneurysm neck, after which the prosthesis may be fully unsheathed and detached from the delivery device using a number of techniques such as those described in more detail below. This is another highly advantageous feature of the present endovascular prosthesis.

The present endovascular prosthesis is believed to be particularly useful in the treatment of aneurysms such as those described hereinabove and is therefore believed to provide a significant alternative to the conventional surgical techniques described hereinabove. Additionally, it is envisaged that the present endovascular prosthesis may be used in the treatment of certain aneurysms which are diagnosed as being inoperable. The present endovascular prosthesis also is believed to provide a significant advantage of current endovascular approaches such as the Guglielmi Detachable Coil described hereinabove. Specifically, since the present endovascular prosthesis does not rely on insertion into the aneurysm of a metal packing material (e.g., platinum coil), the risk of rupturing the aneurysm is mitigated as is the risk of intra-aneurysmal rearrangement of the metal packing material and subsequent reappearance of the aneurysm. Of course, those of skill in the art will recognize that there may be certain situations where the present endovascular prosthesis could be used in combination with Guglielmi Detachable Coils described hereinabove—e.g., to treat an aneurysm with a large neck in which an added structure across the neck (i.e., the present endovascular prosthesis) would help hold the coils with in the aneurysmal sac (this would obviate or mitigate the possibility of a coil exiting the aneurysm sac and causing an ischemic stroke).

BRIEF DESCRIPTION OF THE DRAWINGS

Embodiments of the present invention will be described with reference to the accompanying drawings, wherein like reference numerals denote like parts, and in which.

DETAILED DESCRIPTION OF THE PREFERRED EMBODIMENTS

Figure 1:
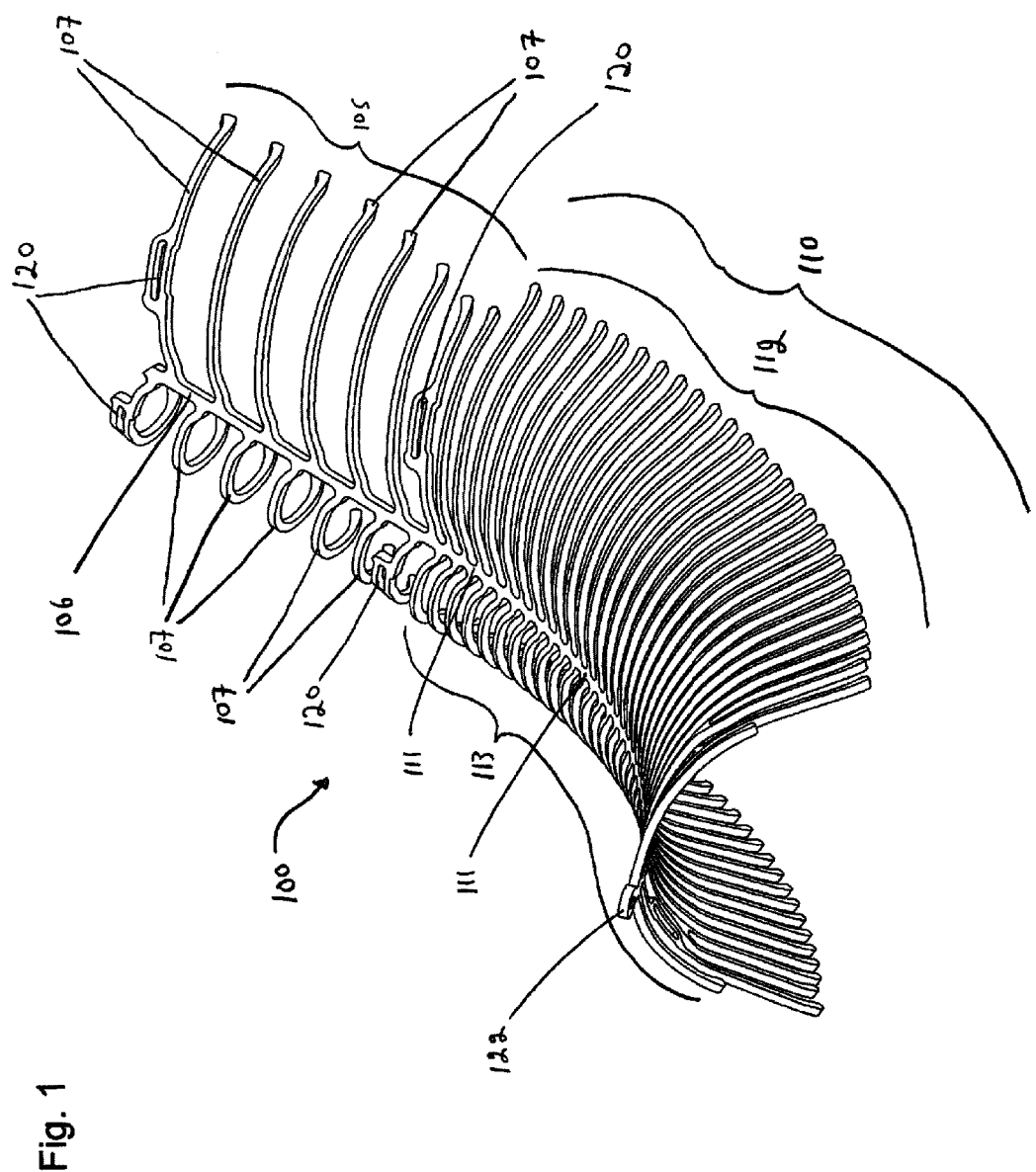
FIG. 1 illustrates a perspective view of a preferred embodiment of the present endovascular prosthesis.

The present invention relates to an endovascular prosthesis comprising: a first expandable portion expandable from a first, unexpanded state to a second, expanded state to urge the first expandable portion against a vascular lumen; and a retractable leaf portion attached to the first expandable portion, the retractable leaf portion comprising at least one spine portion and a plurality of rib portions attached to the spine portion. In one preferred embodiment of the present endovascular prosthesis, the retractable leaf portion is configured such that a pair of ribs attached on opposite sides of a longitudinally straightened configuration of the spine portion in a plane of view normal to a central axis of the prosthesis defines a shape, in two dimensions, that is substantially non-circular. In another preferred embodiment of the present endovascular prosthesis, the retractable leaf portion is configured such that a pair of ribs attached on opposite sides of a longitudinally straightened configuration of the spine portion in a plane of view normal to a central axis of the prosthesis defines a shape, in two dimensions, through which one straight line can be translated from one side to the other side of the shape so as to traverse the shape only once at every point along the shape. Preferred embodiments of this endovascular prosthesis may include any one or a combination of any two or more of any of the following features:

- the shape has a substantially parabolic configuration;
- the shape has a substantially V-shaped configuration;
- the shape has a substantially bell-shaped configuration;
- the shape has a substantially semi-circular shaped configuration;
- the shape has a substantially semi-elliptical shaped configuration;
- the shape comprises a pair of angled straight sections interconnected by a curved section;
- longitudinally adjacent pairs of rib portions are free of interconnecting struts;
- a single spine portion is connected to the first expandable portion;
- the single spine portion comprises a row of rib portions connected to one side of the single spine portion;
- the single spine portion comprises a pair of rows of rib portions, each row of rib portions connected to one side of the single spine portion;
- the single spine portion comprises a pair of rows of rib portions connected to opposed sides of the single spine portion;
- in two dimensions, each row of rib portions is a substantial mirror image of an adjacent row of rib portions along the single spine portion
- a first row of rib portions is connected at a plurality of first connection points to the single spine portion and a second row of rib portions is connected at a plurality of second connection points to the single spine portion, the plurality of first connection points and the plurality of second connection points being longitudinally aligned with respect to one another;
- a first row of rib portions is connected at a plurality of first connection points to the single spine portion and a second row of rib portions is connected at a plurality of second connection points to the single spine portion, the plurality of first connection points and the plurality of second connection points being longitudinally staggered with respect to one another;
- the single spine portion is linear;
- the single spine portion is curvilinear;
- the single spine portion is curved;
- the single spine portion comprising an undulating pattern comprising alternating peaks and valleys;
- at least some rib portions are connected to the peaks in the undulating pattern;
- each rib portion is connected to a peak in the undulating pattern;
- in two dimensions, each rib portion is configured substantially to form an acute angle with respect to a spine central axis of the single spine portion;
- in two dimensions, each rib portion comprises a rib proximal portion, a rib distal portion and a rib intermediate portion disposed therebetween;
- in two dimensions, each rib portion has a substantially constant circumferential width;
- in two dimensions, each rib portion has a variable circumferential width;
- in two dimensions, the rib intermediate portion has a circumferential width less than at least one of the rib proximal portion and the rib distal portion;
- in two dimensions, the rib intermediate portion has a circumferential width less than both of the rib proximal portion and the rib distal portion;
- the rib proximal portion has a circumferential width in the range of from about 0.0010 to about 0.0075 inches;
- the rib proximal portion has a circumferential width in the range of from about 0.0016 to about 0.0054 inches;
- the rib proximal portion has a circumferential width in the range of from about 0.0022 to about 0.0033 inches;
- the rib proximal portion is from about 1% to about 10% of the overall length of the rib portion;
- the rib proximal portion is from about 2% to about 6% of the overall length of the rib portion;
- the rib proximal portion is about 3% of the overall length of the rib portion;
- the rib intermediate portion has a circumferential width in the range of from about 0.0005 to about 0.0100 inches;
- the rib intermediate portion has a circumferential width in the range of from about 0.0011 to about 0.0062 inches;
- the rib intermediate portion has a circumferential width in the range of from about 0.0016 to about 0.0024 inches;
- the rib intermediate portion is from about 25% to about 90% of the overall length of the rib portion;
- the rib intermediate portion is from about 60% to about 90% of the overall length of the rib portion;
- the rib intermediate portion is about 90% of the overall length of the rib portion;
- the rib distal portion has a circumferential width in the range of from about 0.0010 to about 0.0120 inches;
- the rib distal portion has a circumferential width in the range of from about 0.0013 to about 0.0072 inches;
- the rib distal portion has a circumferential width in the range of from about 0.0016 to about 0.0024 inches;
- the rib distal portion is up to about 25% of the overall length of the rib portion;
- the rib distal portion is from about 4% to about 16% of the overall length of the rib portion;

the rib distal portion is up to about 7% of the overall length of the rib portion;
the rib proximal portion is configured to form a rib proximal portion acute angle with respect to a central axis of the endovascular prosthesis;
the rib proximal portion acute angle is in the range of from about 15° to about 90°;
the rib proximal portion acute angle is in the range of from about 35° to about 60°;
the rib proximal portion acute angle is about 45°
the rib distal portion is configured to form a rib distal portion angle with respect to a rib intermediate portion of the endovascular prosthesis;
the rib distal portion angle is in the range of from about 0° to about 120°;
the rib distal portion angle is in the range of from about 3° to about 60°;
the rib distal portion angle is about 8°;
the rib intermediate portion is configured to form a rib intermediate portion acute angle with respect to a central axis of the endovascular prosthesis;
the rib intermediate portion acute angle is in the range of from about 5° to about 140°;
the rib intermediate portion acute angle is in the range of from about 22° to about 86°;
the rib intermediate portion acute angle is about 45°;
the rib intermediate portion comprises: (i) a rib intermediate first portion connected to the rib proximal portion and configured to form a rib intermediate first portion acute angle with respect to a central axis of the endovascular prosthesis, and (ii) a rib intermediate second portion connected to the rib distal portion and configured to form a rib intermediate second portion acute angle with respect to a central axis of the endovascular prosthesis;
the rib intermediate first portion acute angle is less than the rib intermediate second portion acute angle;
the rib intermediate first portion acute angle is in the range of from about 5° to about 140°;
the rib intermediate first portion acute angle is in the range of from about 22° to about 66°;
the rib intermediate first portion acute angle is about 30°;
the rib intermediate second portion acute angle is in the range of from about 5° to about 140°;
the rib intermediate second portion acute angle is in the range of from about 42° to about 86°;
the rib intermediate second portion acute angle is about 60°;
the rib intermediate first portion has a circumferential width in the range of from about 0.0010 to about 0.0100 inches;
the rib intermediate first portion has a circumferential width in the range of from about 0.0014 to about 0.0062 inches;
the rib intermediate first portion has a circumferential width in the range of from about 0.0018 to about 0.0024 inches;
the rib intermediate first portion is from about 5% to about 25% of the overall length of the rib portion;
the rib intermediate first portion is from about 7% to about 17% of the overall length of the rib portion;
the rib intermediate first portion is about 9% of the overall length of the rib portion;
the rib intermediate second portion has a circumferential width in the range of from about 0.0005 to about 0.0070 inches;
the rib intermediate second portion has a circumferential width in the range of from about 0.0011 to about 0.0044 inches;
the rib intermediate second portion has a circumferential width in the range of from about 0.0016 to about 0.0018 inches;
the rib intermediate second portion is from about 25% to about 90% of the overall length of the rib portion;
the rib intermediate second portion is from about 53% to about 85% of the overall length of the rib portion;
the rib intermediate second portion is about 81% of the overall length of the rib portion;
in two dimensions, the rib distal portion of each rib portion is directed away from the first expandable portion;
in two dimensions, the rib distal portion of each rib portion is directed toward the first expandable portion;
in two dimensions, each rib portion is linear;
in two dimensions, each rib portion is curvilinear;
in two dimensions, each rib portion is curved;
in two dimensions, each rib portion comprises at least two sub-portions each sub-portion form a different angle with respect to a central axis of the endovascular prosthesis;
a pair of longitudinally adjacent rib portions are spaced at a connection point to the spine portion at a distance ranging from about 0.0254 mm to about 10 mm.
a pair of longitudinally adjacent rib portions are spaced at a connection point to the spine portion at a distance ranging from about 0.0254 mm to about 5 mm;
a pair of longitudinally adjacent rib portions are spaced at a connection point to the spine portion at a distance ranging from about 0.1400 mm to about 3 mm;
a pair of longitudinally adjacent rib portions are spaced at a connection point to the spine portion at a distance ranging from about 0.1400 mm to about 1 mm;
a pair of longitudinally adjacent rib portions are spaced at a connection point to the spine portion at a distance ranging from about 0.1400 mm to about 0.8 mm;
a pair of longitudinally adjacent rib portions are spaced at a connection point to the spine portion at a distance ranging from about 0.1400 mm to about 0.6 mm;
a pair of longitudinally adjacent rib portions are spaced at a connection point to the spine portion at a distance of about 0.254 mm;
in two dimensions, the at least one spine portion and the plurality of rib portions attached to the spine portion combine to occupy less than about 75% of a surface area of the retractable leaf portion;
in two dimensions, the at least one spine portion and the plurality of rib portions attached to the spine portion combine to occupy from about 5% to about 75% of a surface area of the retractable leaf portion;
in two dimensions, the at least one spine portion and the plurality of rib portions attached to the spine portion combine to occupy from about 5% to about 65% of a surface area of the retractable leaf portion;
in two dimensions, the at least one spine portion and the plurality of rib portions attached to the spine portion combine to occupy from about 10% to about 50% of a surface area of the retractable leaf portion;
in two dimensions, the at least one spine portion and the plurality of rib portions attached to the spine portion combine to occupy from about 15% to about 40% of a surface area of the retractable leaf portion;
in two dimensions, the at least one spine portion and the plurality of rib portions attached to the spine portion combine to occupy less than about 10% of a surface area of the retractable leaf portion;

in two dimensions, the at least one spine portion and the plurality of rib portions attached to the spine portion combine to occupy less than about 8% of a surface area of the retractable leaf portion;

in two dimensions, the at least one spine portion and the plurality of rib portions attached to the spine portion combine to occupy less than about 5% of a surface area of the retractable leaf portion;

in two dimensions, the at least one spine portion and the plurality of rib portions attached to the spine portion combine to occupy less than about 3% of a surface area of the retractable leaf portion;

the retractable leaf portion further comprises a cover layer connected to the plurality of rib portions;

the retractable leaf portion comprises less than 10 longitudinally spaced rib portions connected on one side of the spine portion;

the retractable leaf portion comprises less than 8 longitudinally spaced rib portions connected on one side of the spine portion;

the retractable leaf portion comprises less than 6 longitudinally spaced rib portions connected on one side of the spine portion;

the retractable leaf portion contains only 3 longitudinally spaced rib portions connected on one side of the spine portion;

the at least one spine portion is curved about an axis transverse to a central axis of the endovascular prosthesis;

the at least one spine portion is curved about an axis substantially orthogonal to a central axis of the endovascular prosthesis;

the axis is opposed to the plurality of rib portions relative to the at least one spine portion;

the at least one spine portion comprises a first radius of curvature over the length of the at least one spine portion about an axis transverse to a central axis of the endovascular prosthesis;

the first radius of curvature is substantially constant from a proximal portion of the at least one spine portion to a distal portion of the at least one spine portion;

the first radius of curvature is variable from a proximal portion of the at least one spine portion to a distal portion of the at least one spine portion;

the first radius of curvature decreases from a proximal portion of the at least one spine portion to a distal portion of the at least one spine portion;

the retractable leaf portion comprises a second radius of curvature over the length of the at least one spine portion about a central axis of the endovascular prosthesis;

the second radius of curvature is substantially constant from a proximal portion of the retractable portion to a distal portion of the retractable portion;

the second radius of curvature is variable from a proximal portion of the retractable leaf portion to a distal portion of the retractable leaf portion;

the second radius of curvature increases from a proximal portion of the retractable leaf portion to a distal portion of the retractable leaf portion;

the first expandable portion has a diameter in the second, expanded state in range of from about 1.5 mm to about 40 mm;

the first expandable portion has a diameter in the second, expanded state in range of from about 1.5 mm to about 30 mm;

the first expandable portion has a diameter in the second, expanded state in range of from about 1.5 mm to about 20 mm;

the first expandable portion has a diameter in the second, expanded state in range of from about 1.5 mm to about 10 mm;

the first expandable portion has a diameter in the second, expanded state in range of from about 2.5 mm to about 5 mm;

a single spine portion is connected to the first expandable portion and a loop portion is connected to a distal portion of the single spine portion;

a single spine portion is connected to the first expandable portion and a split loop portion connected to a distal portion of the single spine portion;

the loop portion comprises a radioopaque portion;

the endovascular prosthesis further comprises a second expandable portion expandable from a first, unexpanded state to a second, expanded state to urge the first expandable portion against a vascular lumen the second expandable portion comprises a radioopaque portion;

the prosthesis is manufactured from a starting material having a thickness in the range of from about 0.0005 to about 0.0200 inches;

the prosthesis is manufactured from a starting material having a thickness in the range of from about 0.0015 to about 0.0100 inches;

the prosthesis is manufactured from a starting material having a thickness in the range of from about 0.0020 to about 0.0030 inches;

the starting material is in tubular configuration;

the starting material is in flat configuration;

the endovascular prosthesis is manufactured from a tubular starting material on which a cutting technique has been applied;

the endovascular prosthesis is manufactured from a flat starting material on which a cutting technique has been applied;

the cutting technique comprises a laser cutting technique;

the cutting technique comprises a chemical etching technique;

the first expandable portion comprises a radioopaque portion;

the prosthesis is constructed from a self-expanding material;

the prosthesis is constructed from a shape memory alloy;

the prosthesis is constructed from nitinol;

the prosthesis is constructed from a metallic material; and/or the prosthesis is constructed from a polymer material (e.g., a bioabsorbable material, a biodegradable material, a shape memory polymer and the like).

Figure 2:
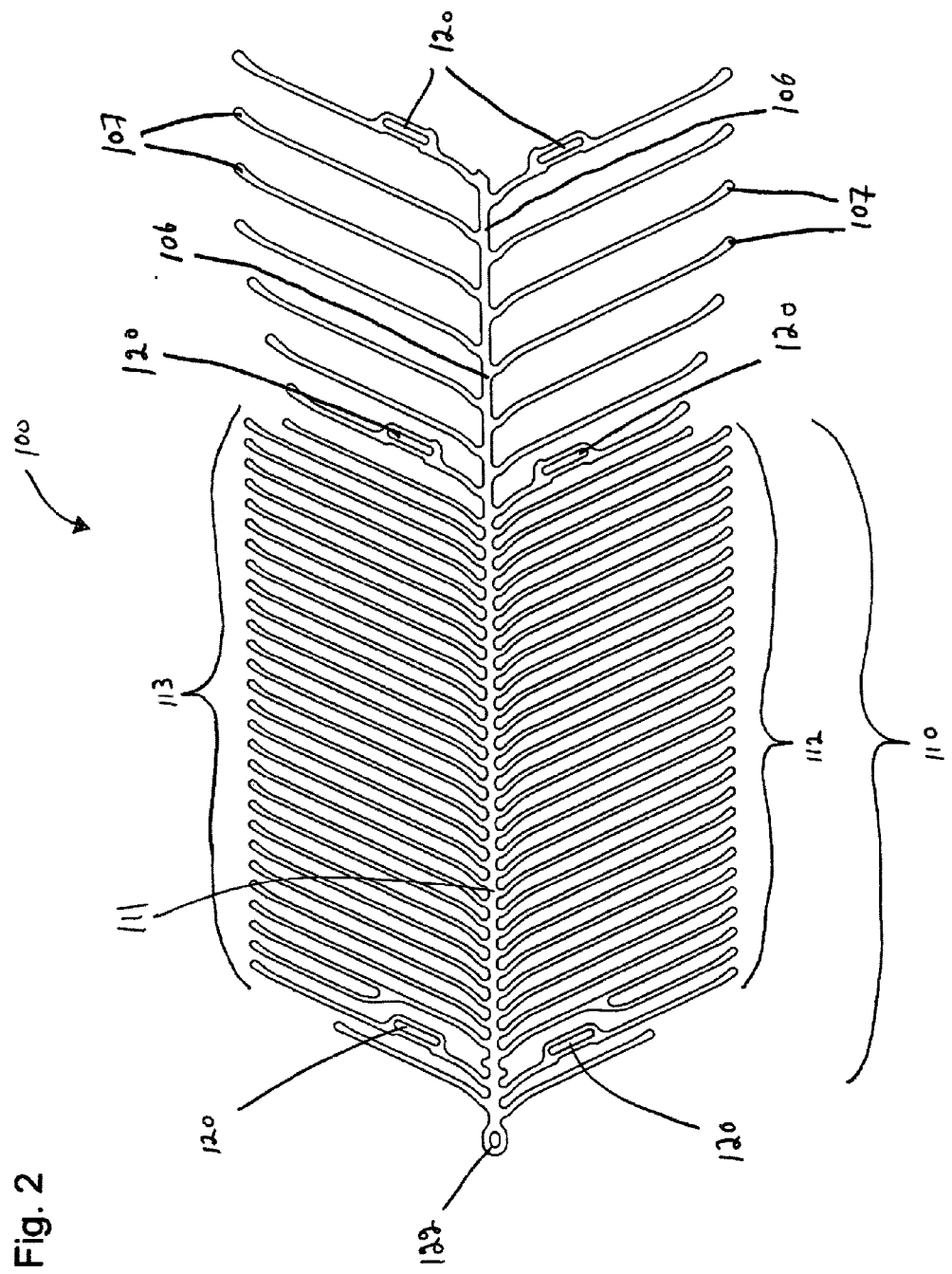
FIG. 2 is a two-dimensional representation of the endovascular prosthesis illustrated in FIG. 1.

With reference to FIGS. 1-2, there is illustrated an endovascular prosthesis 100. Endovascular prosthesis 100 comprises an expandable anchor portion 105 and a leaf portion 110 and a loop portion 122. Expandable anchor portion 105 comprises an anchor spine 106 with a series of anchor ribs 107 disposed on opposite sides of anchor spine 106.

Leaf portion 110 comprises a spine portion 111 to which is connected a first row of rib portions 112 on one side thereof and a second row of rib portions 113 on an opposed side thereof. As can be seen, spine portion 111 comprises an undulating configuration (see also FIG. 3 for an enlarged view of this feature). Individual ribs in each of rows 112,113 are connected to the peaks of the undulating pattern formed by spine portion 111. This results in the connection points of individual rib portions in rows 112,113 being longitudinally offset with respect to one another.

The specifications for each rib portion in rows 112 and 113 are preferred to be those mentioned above.

Endovascular prosthesis 100 further comprises a series of radioopaque markers anchor spots 120 (the radioopaque material is not shown for clarity) disposed at various positions on prosthesis 100.

Leaf portion 110 has connected thereto a loop portion 122 for connection to a delivery system.

Figure 3:
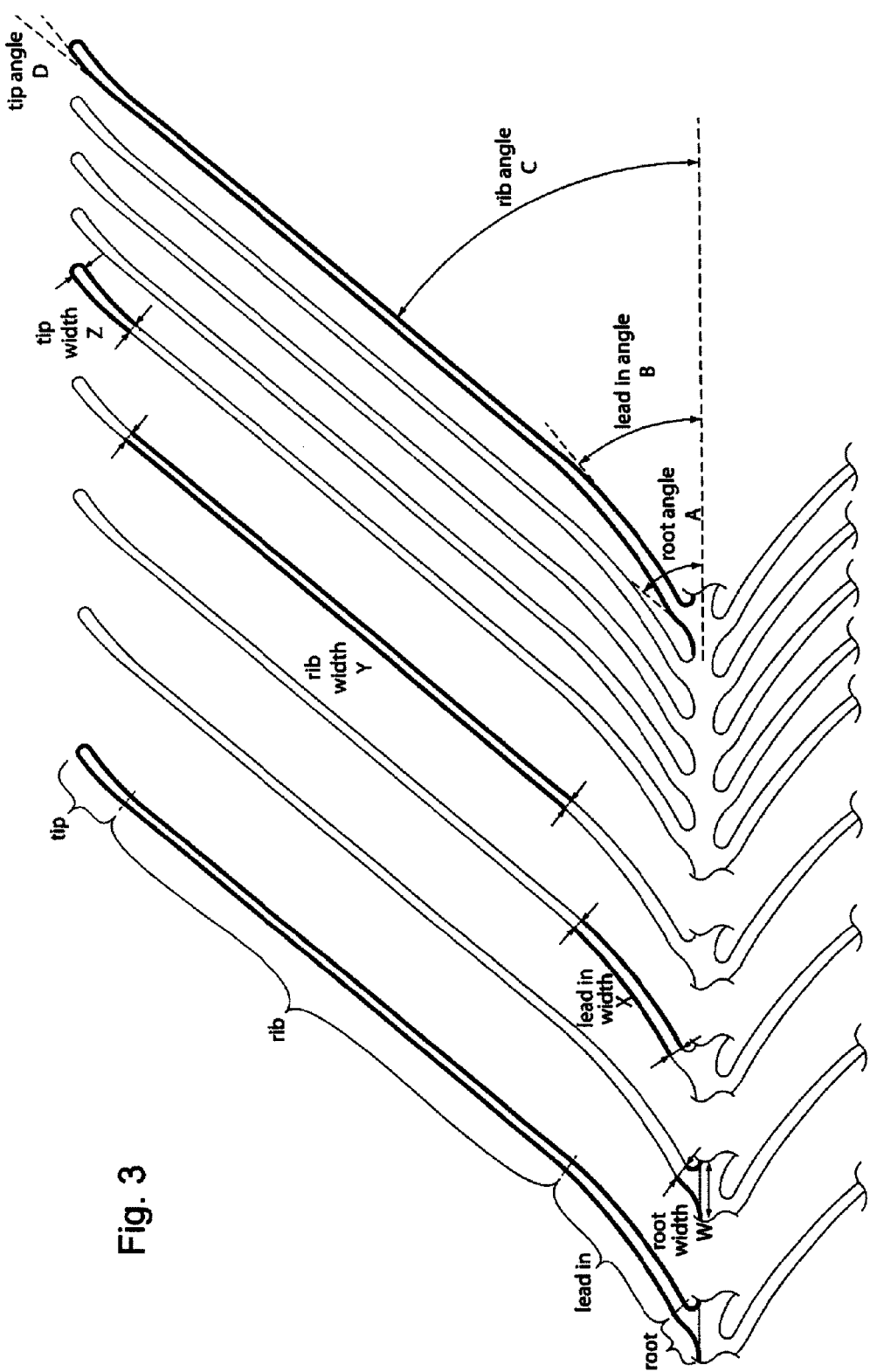
FIG. 3 is an enlarged view of a portion of FIG. 2 identifying various elements in the design of the endovascular prosthesis.

With reference to FIG. 3, there is illustrated an enlarged view of a portion of endovascular device 100. The following is a concordance of terms used in FIG. 3 and elsewhere in this specification:

| | | |
|---|---|---|
| A | root angle | rib proximal portion acute angle |
| B | lead in angle | rib intermediate first portion acute angle |
| C | rib angle | rib intermediate second portion acute angle |
| D | tip angle | rib distal portion acute angle |
| W | root width | rib proximal portion |
| X | lead in width | rib intermediate first portion |
| Y | rib width | rib intermediate second portion |
| Z | tip width | rib distal portion |

Figure 4:
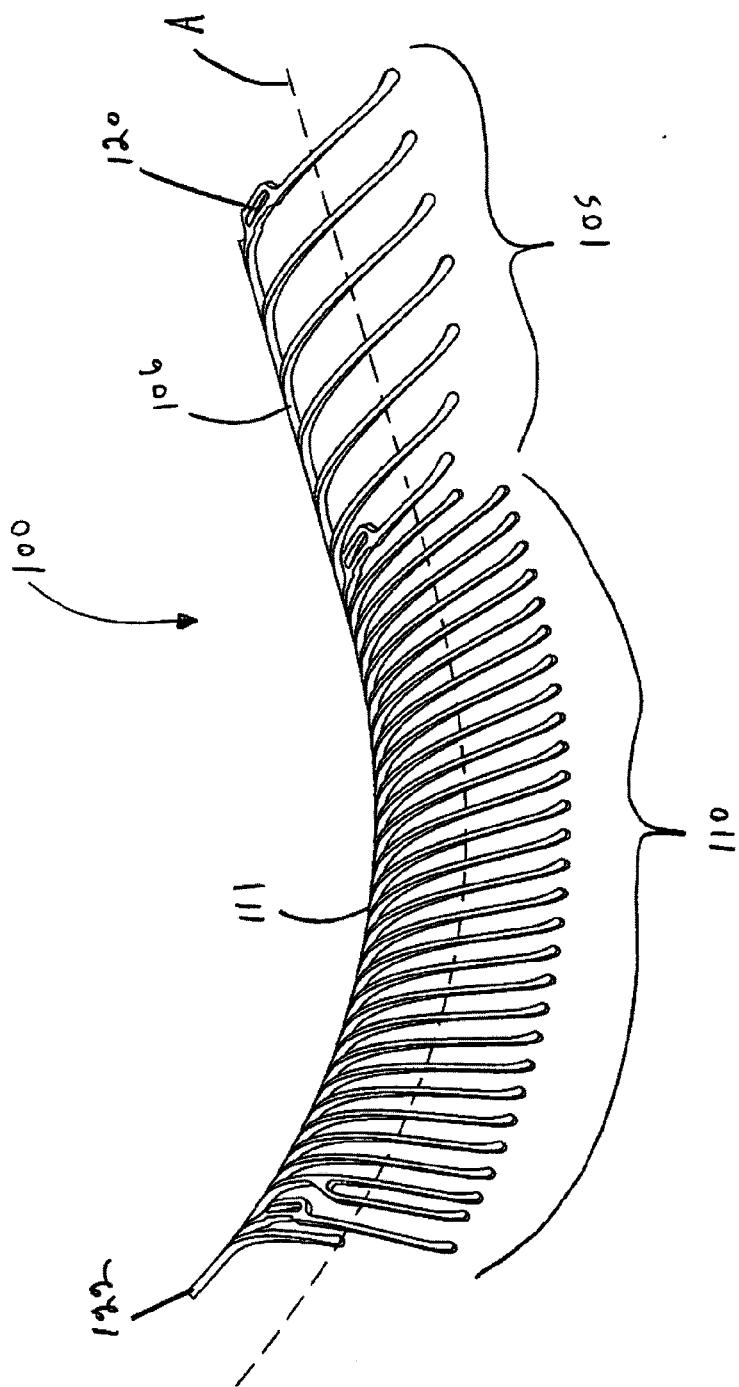
FIG. 4 illustrates a side elevation of the prosthesis illustrated in FIG. 1.

With reference to FIG. 4, there is illustrated a side elevation of endovascular prosthesis 100. As shown, spine portion 111 and anchor spine 106 are combined/configured to create a curved spine for the entire endovascular prosthesis 100. The axis of curvature is normal to a central axis A of endovascular prosthesis 100.

Figure 5:
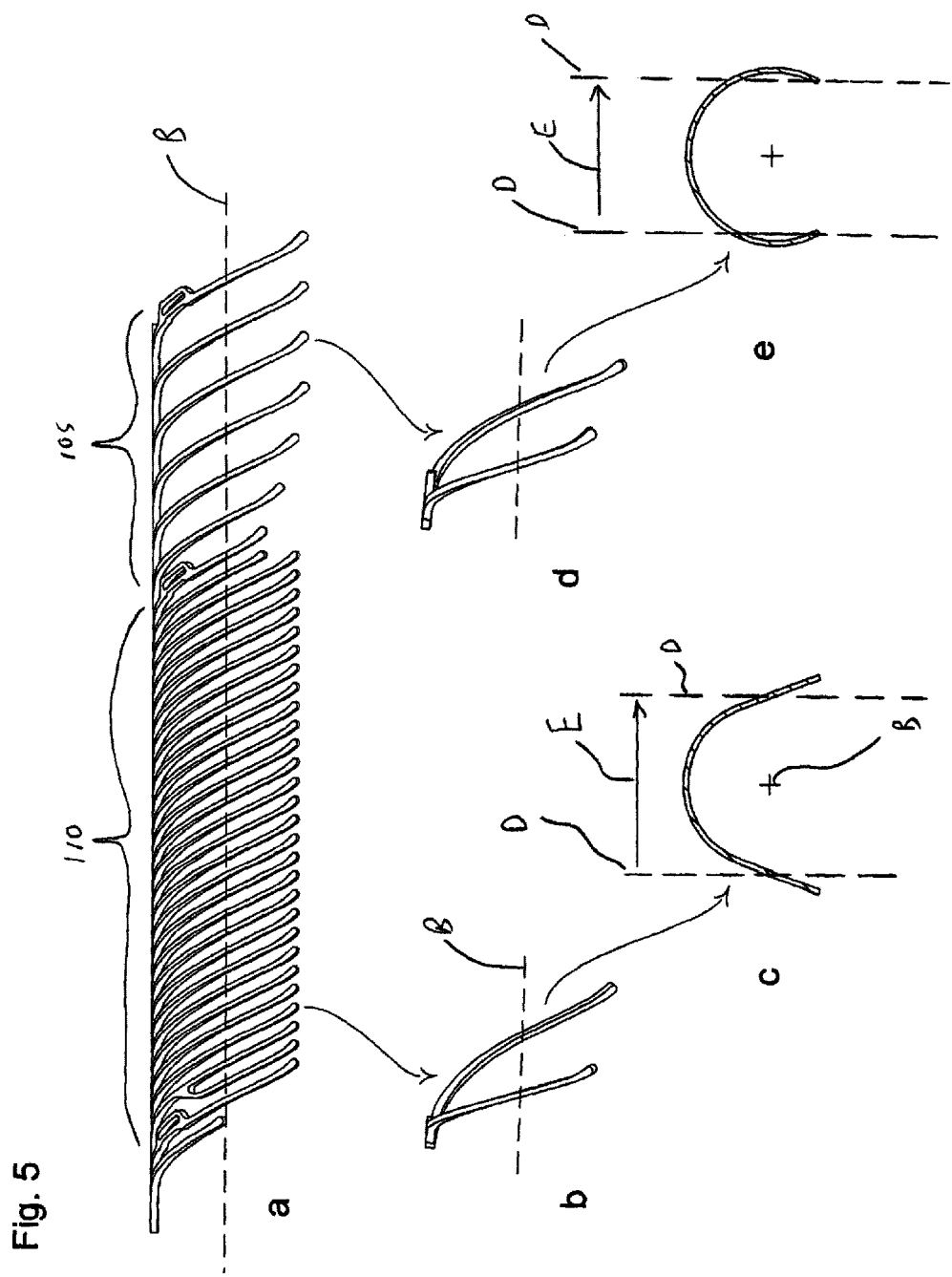
FIG. 5 illustrates the sequential derivation of various end views of the prosthesis illustrated in FIG. 4.

With reference to FIG. 5, there is illustrated an important feature of a preferred embodiment of the present endovascular prosthesis.

As described above, in an preferred embodiment of the present invention, the retractable leaf portion is configured such that a pair of ribs attached on opposite sides of a longitudinally straightened configuration of the spine portion in a plane of view normal to a central axis of the prosthesis defines a shape, in two dimensions, through which one straight line can be translated from one side to the other side of the shape so as to traverse the shape only once at every point along the shape. An example of this feature is what is illustrated in FIG. 5.

Thus, it can be seen that the curved spine of prosthesis 100 illustrated in FIG. 4 has been straightened to generate a longitudinal axis B—see FIG. 5a. Such straightening is within the purview of a person of ordinary skill in the art.

Next, the pair of rib portions on opposite sides of spine portion 111 in expandable anchor portion 110 is isolated—see FIG. 5b. The isolated pair of ribs shown in FIG. 5b is a three dimensional object. When this three dimensional object is viewed along longitudinal axis B, the resulting two dimensional representation is shown in FIG. 5c.

As can be seen with reference to FIG. 5c, when a line D is translated from one side of the pair of ribs shown in FIG. 5c in the direction of arrow E, line D traverses the shape corresponding to the pair of ribs only once at every point along the shape (i.e., line D does not traverse the shape of the pair of ribs at two locations at any one point along the shape). It is this feature of the present endovascular prosthesis which affords the advantage of an improved rotational range of correct placement of the device as will be described below with reference to FIG. 8.

With continued reference to FIG. 5, a similar rendering of shape development has been done with reference to anchor ribs 105—see FIGS. 5d and 5e. In this case, when line D is moved in the direction of arrow E, line D traverses the shape resulting from a two dimensional representation of the pair of ribs in at least two points along the shape. Thus, the shape shown in FIG. 5e would not be suitable for use in retractable leaf portion 110 of endovascular prosthesis 100. It is, of course, suitable for use in anchor portion 105 since this is not used to occlude the aneurysm.

Figure 10:
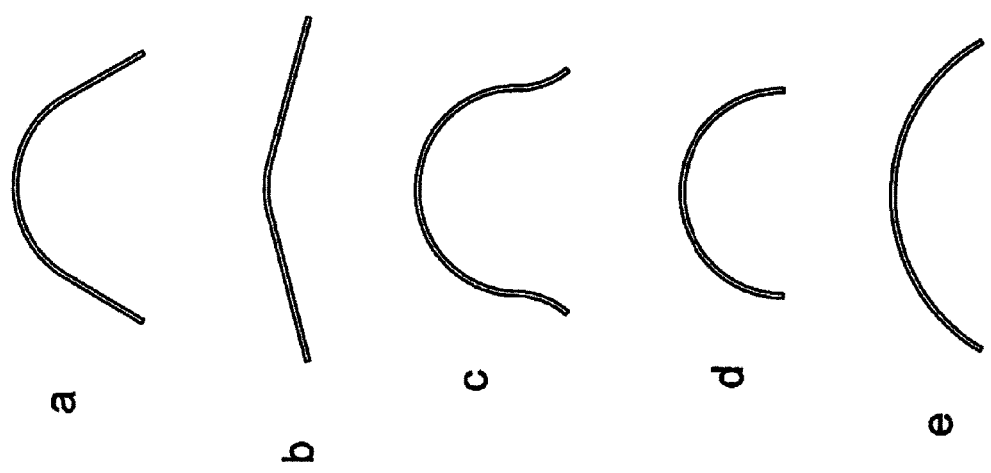
FIG. 10 illustrates various end view embodiments of the design of the retractable leaf portion of the present endovascular prosthesis.

FIG. 10 illustrates various shapes derived in the manner of FIG. 5a that can be used in the present endovascular prosthesis (in this regard, the shapes in FIGS. 5c and 10a are identical). The characterizing feature of the shape shown in FIGS. 5c/10a can be seen in FIGS. 10b, 10c, 10d and 10e (i.e., when line D is translated from one side of the pair of ribs shown in FIG. 5c in the direction of arrow E, line D traverses the shape corresponding to the pair of ribs only once at every point along the shape).

Figure 6:
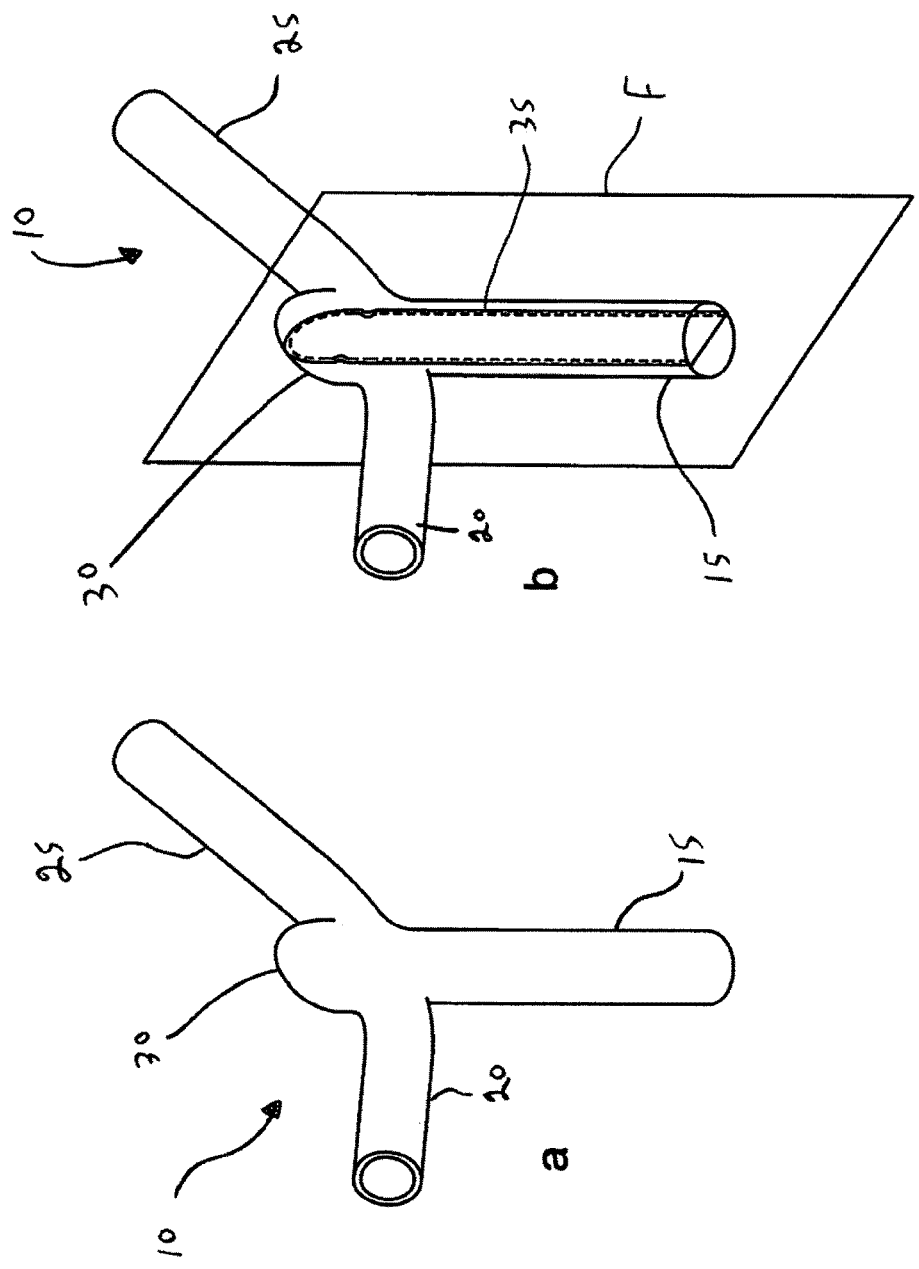
FIGS. 6 and 7 illustrate the vasculature of a bifurcated artery afflicted with an aneurysm.

With reference to FIG. 6a, there is illustrated a perspective view of a bifurcated artery 10. Bifurcated artery 10 comprises a primary passageway 15 and a pair of secondary passageways 20,25. An aneurysm 30 is shown at a junction between passageways 15,20,25 of bifurcated artery 10.

Figure 7:
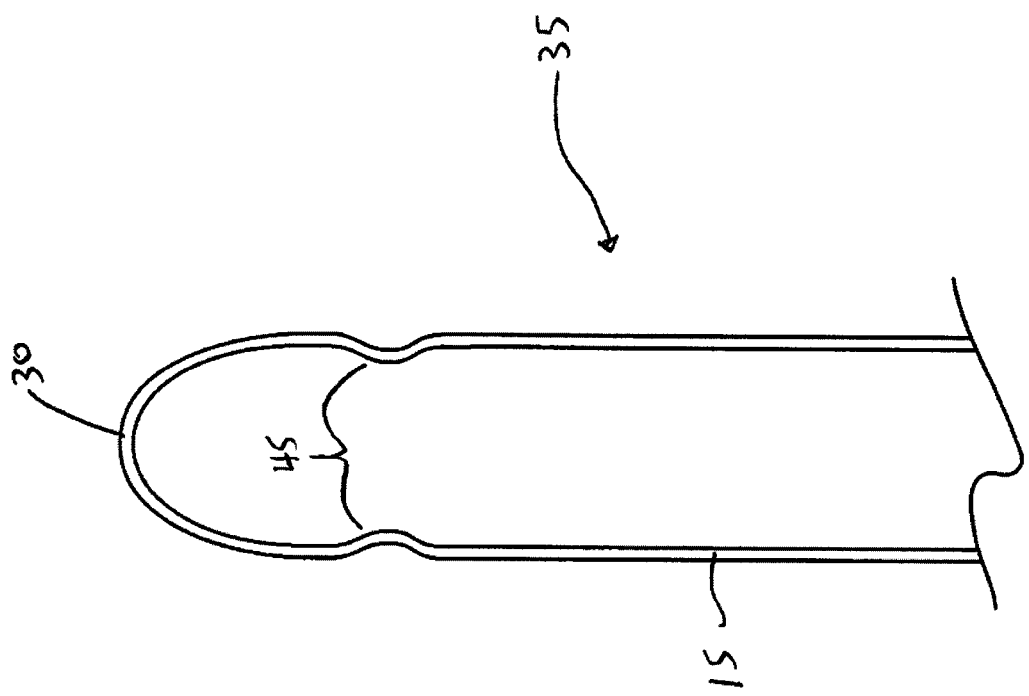

With reference to FIG. 6b, a plane F is shown which bisects secondary passageways 20,25 by bifurcated artery 10. Plane F corresponds to the so-called Sagittal plane of the artery and results in a cross-section 35 that is illustrated in FIG. 7. As can be seen in FIG. 7, aneurysm 30 has an aneurysmal opening 45 which is in communication with primary passageway 15 and secondary passageways 20,25 (not shown in FIG. 7).

Figure 8:
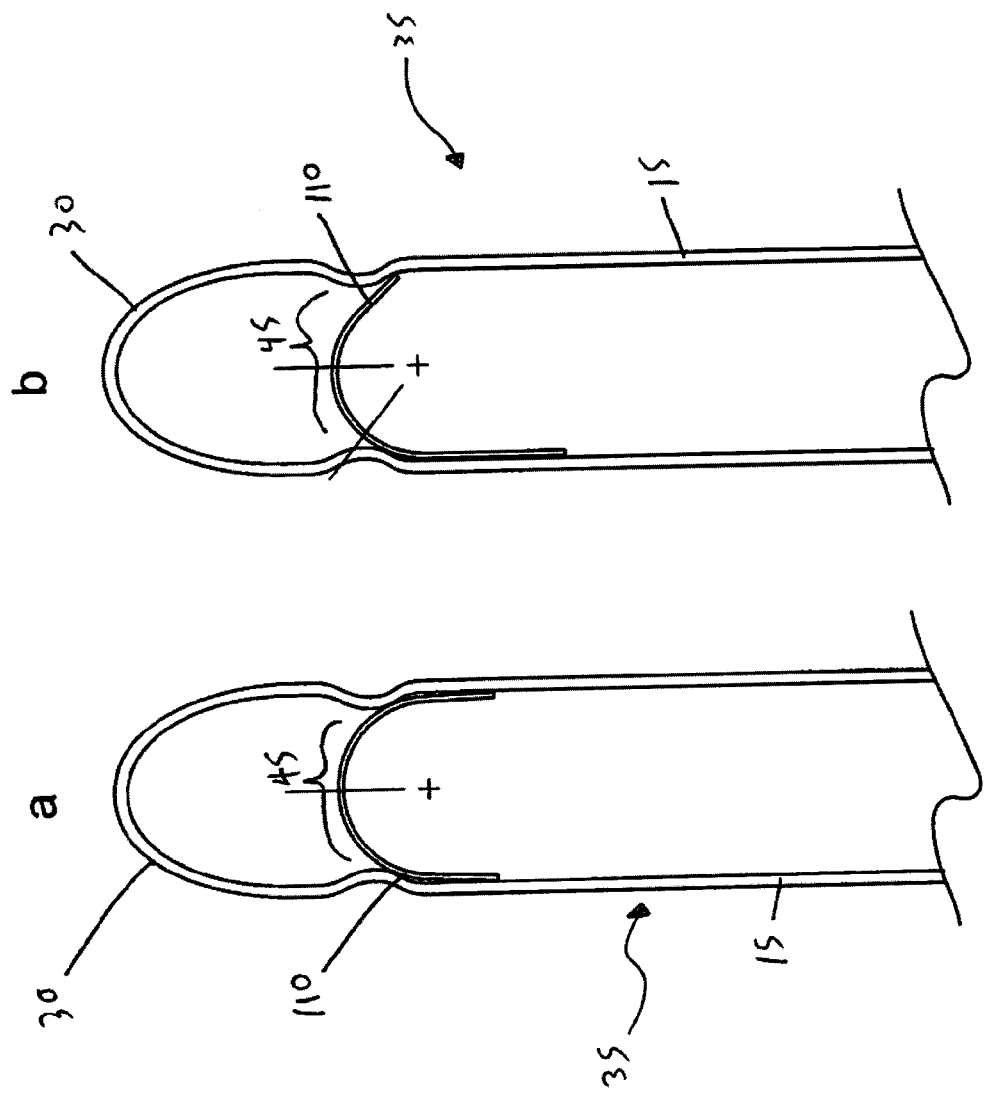
FIG. 8 illustrates the rotational range of implantation of the prosthesis illustrated in FIGS. 1-5.

With reference to FIG. 8, there is shown implantation of endovascular prosthesis 100 in bifurcated artery 10. The focus in FIG. 8 is on the orientation of retractable leaf portion 110. As can be seen in FIG. 8a, endovascular prosthesis 100 is perfectly deployed insofar as retractable leaf portion 110 has an axis of symmetry that is substantially aligned with an axis of symmetry of cross-section 35 of bifurcated artery 10.

With reference to FIG. 8b, it can be seen that the axis of symmetry of retractable leaf portion 110 is rotated with respect to the longitudinal axis of cross-section 35 of bifurcated artery 10. Notwithstanding this, aneurysmal opening 45 is still adequately occluded by retractable leaf portion 110. In addition, the distal portions of retractable leaf portion 110 do not project into primary passageway 15 which otherwise would create potential for thrombosis or other unwanted side effects.

Figure 9:
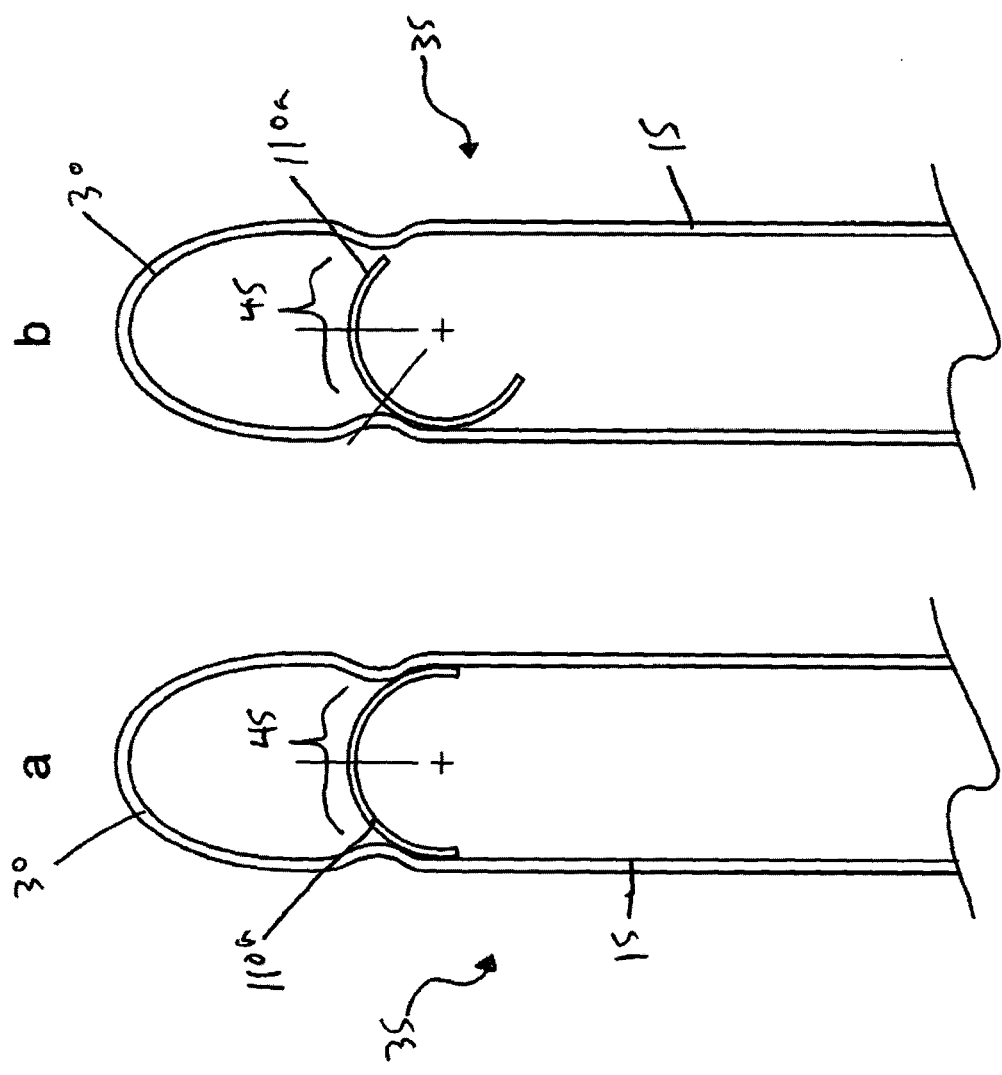
FIG. 9 illustrates the implantation of an endovascular prosthesis with limited rotational range.

A comparative situation is illustrated in FIG. 9. Specifically, FIG. 9 illustrates implantation of endovascular prosthesis 100 where retractable leaf portion 110 has been modified such that a pair of opposed pair of rib portions has a shape, in two dimensions, similar to that shown in FIG. 5e. In FIG. 9a, endovascular prosthesis is perfectly implanted and an aneurysmal opening 45 is properly occluded. In contrast, when the axis of symmetry of retractable leaf portion 110a is rotated with respect to a longitudinal axis of cross-section 35 of bifurcated artery 10, two problems result. First, aneurysmal opening 45 is not properly occluded since, there is insufficient coverage of the vessel wall by one distal portion retractable leaf portion 110a. Second, the other distal portion of retractable leaf portion 110a is protruding into primary passageway 15 thereby causing the potential for thrombosis or other unwanted side effects.

With reference to FIGS. 11-16, there is illustrated delivery and deployment of endovascular prosthesis 100 in a bifurcated artery 10. As can be seen, bifurcated artery 10 comprises an aneurysm 30 having an aneurysmal opening 45.

Of particular note in FIGS. 11-16 is the general manner in which endovascular prosthesis is oriented during delivery and deployment. Specifically, when endovascular prosthesis 100 delivered to bifurcated artery 25, expansible portion 105 is oriented distally with respect to the clinician whereas retractable leaf portion 110 (at the opposed end of endovascular prosthesis with respect to expansible portion 105) is oriented proximally with respect to the clinician thus exiting delivery catheter last.

Figure 11:
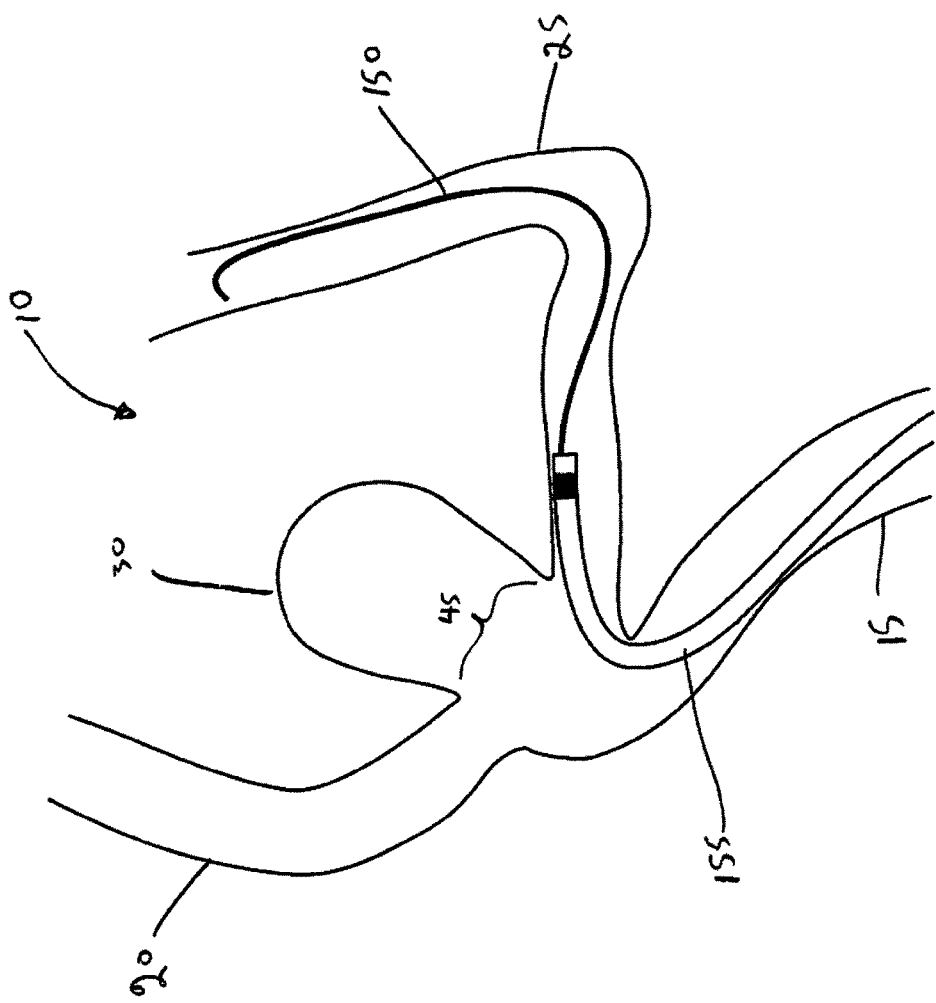
FIGS. 11-16 illustrate, in a step-wise manner, deployment of the endovascular prosthesis illustrated in FIGS. 1-5 in an aneurysm located at the junction of a bifurcated artery.

With reference to FIG. 11, a guidewire 150 and delivery catheter/sheath 155 are inserted and passed through a primary passageway 25 of bifurcated artery 10 in a conventional manner.

Figure 12:
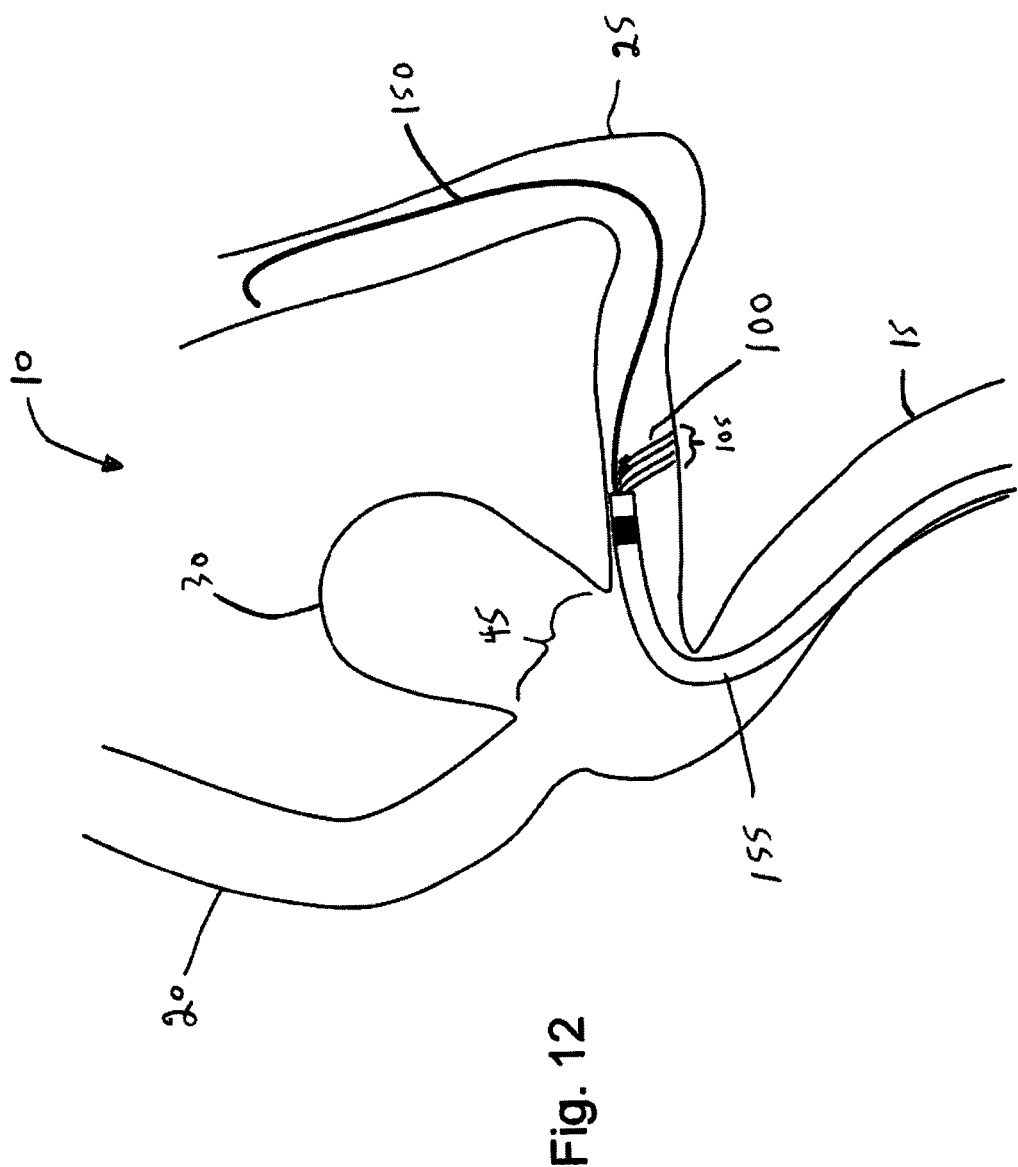

Next, with reference to FIG. 12 endovascular prosthesis 100 attached to a delivery device 200 (not shown in FIGS. 11-12) such as the one described in Tippett referred to above is fed through delivery catheter/sheath 155 until endovascular prosthesis 100 is positioned in secondary passageway 25 of bifurcated artery 10. In other words, delivery catheter/sheath 155 is partially retracted: this results in initial deployment of expansible portion 105 of endovascular prosthesis 100. If the physician is not satisfied with this initial deployment of expansible portion 105 of endovascular prosthesis 100, he/she may re-sheath endovascular prosthesis 100 in an attempt to reposition it within secondary passageway 25 of bifurcated artery 10—see Tippett referred to above for more detail on this feature of endovascular prosthesis 100.

Figure 13:
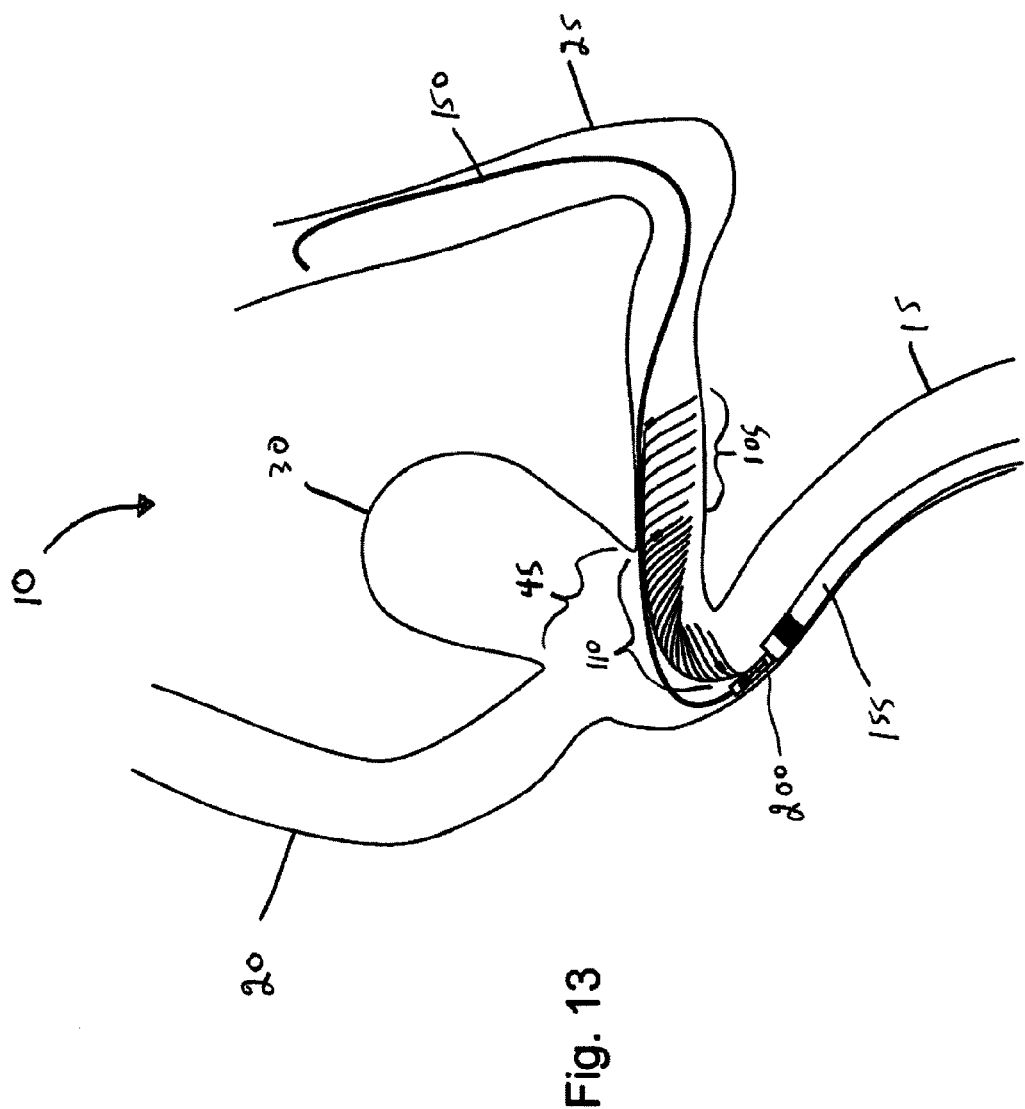

Once the physician is satisfied with the initial deployment of endovascular prosthesis 100, delivery catheter/sheath 155 is further retracted exposing the proximal portion of endovascular prosthesis 100—see FIG. 13 which shows for the first time delivery device 200 referred to above.

Figure 14:
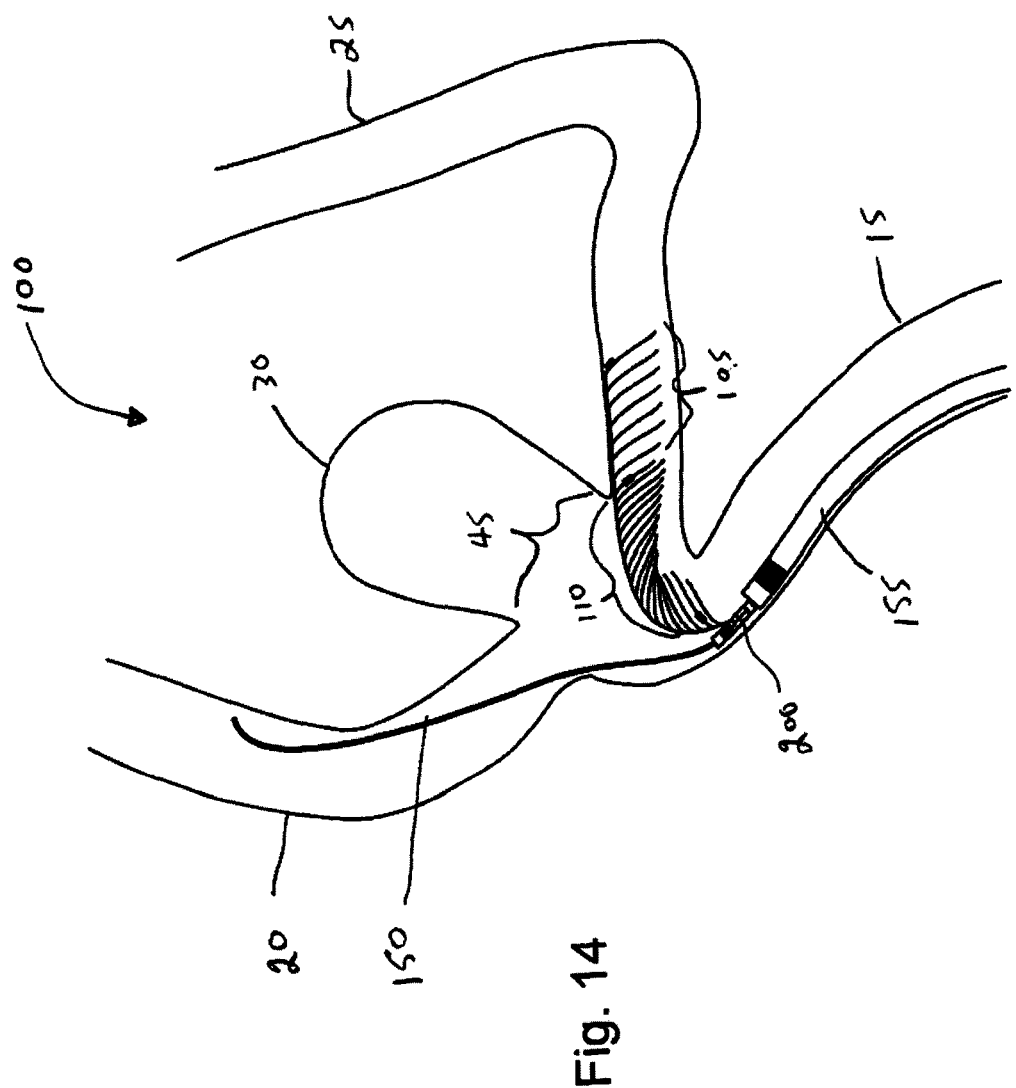
Figure 15:
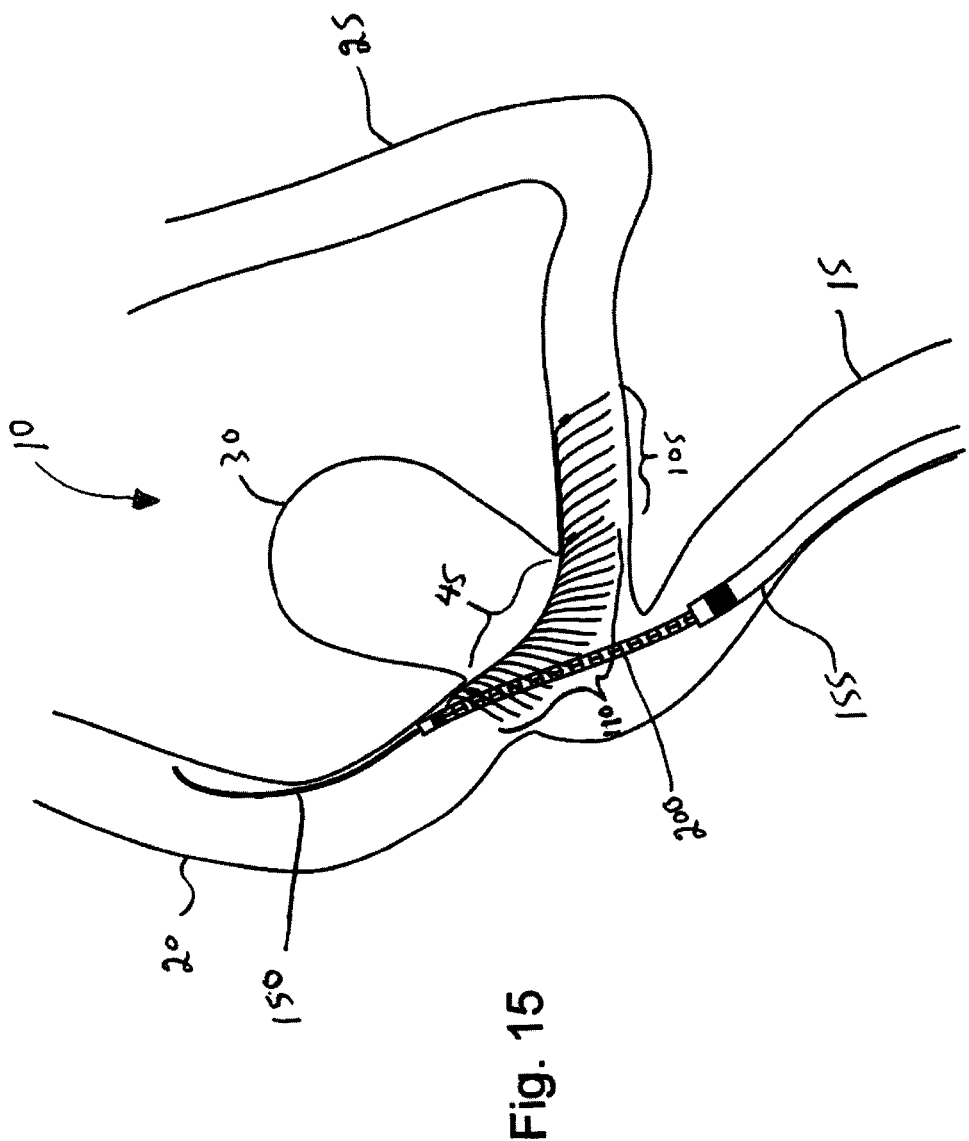

Next, guidewire 150 is retracted from secondary passageway 25 and inserted into secondary passageway 20—see FIG. 14.

After guidewire 150 has been inserted into secondary passageway 20, delivery system 200 is advanced into secondary passageway 20 such that retractable leaf portion 110 of endovascular prosthesis 100 occludes aneurysmal opening 45.

This relatively simplified delivery sequence is an important advantage that accrues at least in part due to the design of endovascular prosthesis 100. As will be appreciated by those of skill in the art, this simplified delivery sequence utilizes a single guidewire 150 to deliver expandable portion 105 of the prosthesis into one of the pair of secondary passageways 20,25 of bifurcated artery 10 and the leaf portion 110 across the aneurysmal opening. This results in the need for a single guidewire and a single delivery system. To the knowledge of the inventors, such a simplified delivery sequence was heretofore unknown.

Figure 16:
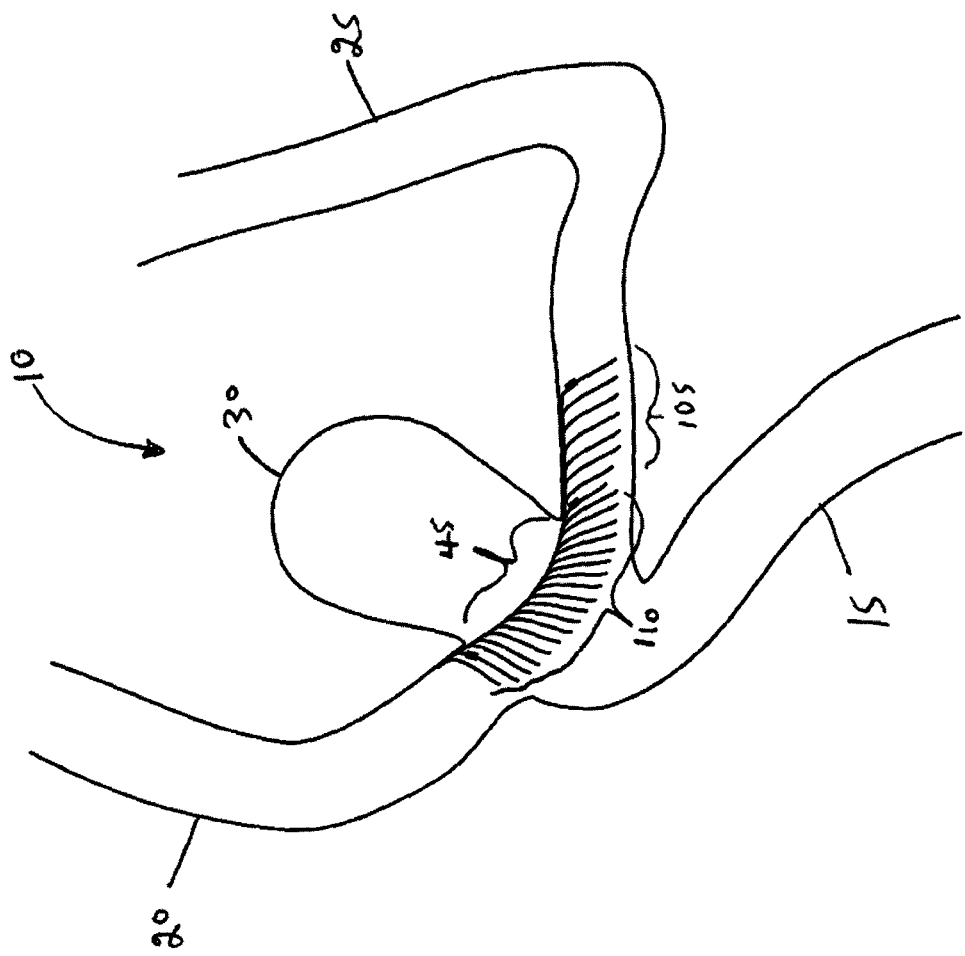

At any time during the delivery and positioning of the endovascular prosthesis, the endovascular prosthesis can be fully recovered/resheathed allowing for repositioning and subsequent unsheathing. Once it has been determined that endovascular prosthesis 100 is in the correct position, delivery device 200 is detached from endovascular prosthesis 100. This can be accomplished in a number manners—see, for example, the various embodiments disclosed in Tippett referred to above. Once this is done, guidewire 150, delivery catheter/sheath 155 and delivery device 200 are withdrawn from bifurcated artery 10 resulting in final deployment of endovascular prosthesis 100 as shown in FIG. 16. In this final deployed configuration, leaf portion 110 of endovascular prosthesis 100 occludes or reduces flow through aneurysmal opening 45 of aneurysm 10.

The endovascular prosthesis of the present invention may further comprise a coating material thereon. The coating material can be disposed continuously or discontinuously on the surface of the prosthesis. Further, the coating may be disposed on the interior and/or the exterior surface(s) of the prosthesis. The coating material can be one or more of a biologically inert material (e.g., to reduce the thrombogenicity of the stent), a medicinal composition which leaches into the wall of the body passageway after implantation (e.g., to provide anticoagulant action, to deliver a pharmaceutical to the body passageway and the like), an expansible/swellable material (e.g., a hydrogel material) and the like.

Further, the present endovascular prosthesis may be provided with a biocompatible coating, in order of minimize adverse interaction with the walls of the body vessel and/or with the liquid, usually blood, flowing through the vessel. A number of such coatings are known in the art. The coating is preferably a polymeric material, which is generally provided by applying to the stent a solution or dispersion of preformed polymer in a solvent and removing the solvent. Non-polymeric coating material may alternatively be used. Suitable coating materials, for instance polymers, may be polytetrafluroethylene or silicone rubbers, or polyurethanes which are known to be biocompatible. Preferably however the polymer has zwitterionic pendant groups, generally ammonium phosphate ester groups, for instance phosphorylcholine groups or analogues thereof.

Examples of suitable polymers are described in International Publication Numbers WO-A-93/16479 and WO-A-93/15775. Polymers described in those documents are hemocompatible as well as generally biocompatible and, in addition, are lubricious. When such coatings are used, it is preferred that the surfaces of the endovascular prosthesis are completely coated in order to minimize unfavourable interactions, for instance with blood, which might lead to thrombosis. This good coating can be achieved by suitable selection of coating conditions, such as coating solution viscosity, coating technique and/or solvent removal step.

The manner by which the present endovascular prosthesis is manufactured is not particularly restricted. Preferably, the endovascular prosthesis is produced by laser cutting or chemical etching techniques applied to a tubular starting material. Thus, the starting material could be a thin tube of a metal or alloy (non-limiting examples include stainless steel, titanium, tantalum, nitinol, Elgiloy, NP35N, cobalt-chromium alloy and mixtures thereof) which would then have sections thereof cut out (by laser cutting or chemical etching) to provide a prosthesis having a pre-determined design. Alternatively, it is possible to cut the design (by laser cutting or chemical etching) of the prosthesis from a flat starting material and thereafter roll the cut product into the desired shape (for example, as illustrated and described above) and heat set in such a configuration.

In a particularly preferred embodiment, the present endovascular prosthesis is made from a suitable material which will expand when a certain temperature is reached. In this embodiment, the material may be a metal alloy (e.g., nitinol) capable of self-expansion at a temperature of at least about 25° C., preferably in the range of from about 25° C. to about 35° C. In this preferred embodiment, it may be desired and even preferable to heat set the endovascular prosthesis to adopt a deployed configuration which has been optimized for the particular intended anatomy—e.g., this is preferred for endovascular prosthesis 100 described above.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. For example, the illustrated embodiments all utilize the leaf portion to act as a so-called flow diverter—i.e., once the device is implanted, the leaf portion diverts blood flow away from entering the aneurysmal opening. In cases where the aneurysmal opening is relatively large, it is possible to modify the leaf portion to act as a retention member—e.g., to retain one or more Guglielmi Detachable Coils in the aneurysm. In this modification, the spacing between adjacent rib portions would be increased a sufficient degree to allow delivery of one or more Guglielmi Detachable Coils through the leaf portion after implantation of the endovascular prosthesis. The Guglielmi Detachable Coils would be less likely to "fall out" of the aneurysm when the leaf portion of the present endovascular prosthesis is covering the aneurysmal opening. Further, while the illustrated embodiments are focussed on treatment of a cerebral aneurysm, it is contemplated that the present endovascular prosthesis may be used to treat other diseases such as aortic disease (e.g., see the discussion of aortic disease set out in International Publication Number WO 02/39924 [Erbel et al.]). In this modification, it may be appropriate to alter several of the above-mentioned dimensions. For example, it is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. An elongate endovascular prosthesis in an unconstrained state, comprising:
   a first expandable portion expandable from a first, unexpanded state to a second, expanded state to urge the first expandable portion against a vascular lumen; and
   a retractable leaf portion attached to the first expandable portion, the retractable leaf portion comprising a single spine portion and a plurality of rib portions attached to the spine portion,
   the retractable leaf portion configured such that a pair of ribs attached on opposite sides of a longitudinally straightened configuration of the spine portion in a plane of view normal to a central axis of the prosthesis defines a shape that, when viewed in two dimensions normal to said central axis of the prosthesis, is substantially non-circular and through which one straight fixed line perpendicular to said axis can be translated from one side to the other side of the shape so as to traverse the shape only once at every point along the shape as the straight fixed line moves from one side of the shape to the other side.

2. The endovascular prosthesis defined in claim 1, wherein the shape has a substantially parabolic configuration.

3. The endovascular prosthesis defined in claim 1, wherein the shape has a substantially V-shaped configuration.

4. The endovascular prosthesis defined in claim 1, wherein the shape has a substantially bell-shaped configuration.

5. The endovascular prosthesis defined in claim 1, wherein the shape has a substantially semi-circular shaped configuration.

6. The endovascular prosthesis defined in claim 1, wherein the shape has a substantially semi-elliptical shaped configuration.

7. The endovascular prosthesis defined in claim 1, wherein the shape comprises a pair of angled straight sections interconnected by a curved section.

8. The endovascular prosthesis defined in claim 1, wherein longitudinally adjacent pairs of rib portions are free of interconnecting struts.

9. The endovascular prosthesis defined in claim 1, wherein the single spine portion comprises a pair of rows of rib portions connected to opposed sides of the single spine portion.

10. The endovascular prosthesis defined in claim 9, wherein a first row of rib portions is connected at a plurality of first connection points to the single spine portion and a second row of rib portions is connected at a plurality of second connection points to the single spine portion, the plurality of first connection points and the plurality of second connection points being longitudinally staggered with respect to one another.

11. The endovascular prosthesis defined in claim 10, wherein the single spine portion comprising an undulating pattern comprising alternating peaks and valleys.

12. The endovascular prosthesis defined in claim 11, wherein each rib portion is connected to a peak in the undulating pattern.

13. The endovascular prosthesis defined in claim 12, wherein, in two dimensions, each rib portion is configured substantially to form an acute angle with respect to a spine central axis of the single spine portion.

14. The endovascular prosthesis defined in claim 13, wherein, in two dimensions, each rib portion comprises a rib proximal portion, a rib distal portion and a rib intermediate portion disposed therebetween.

15. The endovascular prosthesis defined in claim 14, wherein, in two dimensions, each rib portion has a variable circumferential width.

16. The endovascular prosthesis defined in claim 14, wherein, in two dimensions, the rib intermediate portion has a circumferential width less than both of the rib proximal portion and the rib distal portion.

17. The endovascular prosthesis defined in claim 14, wherein the rib proximal portion is from about 2% to about 6% of the overall length of the rib portion.

18. The endovascular prosthesis defined in claim 14, wherein the rib intermediate portion is from about 60% to about 90% of the overall length of the rib portion.

19. The endovascular prosthesis defined in claim 14, wherein the rib distal portion is from about 4% to about 16% of the overall length of the rib portion.

20. The endovascular prosthesis defined in claim 19, wherein the rib proximal portion acute angle is in the range of from about 35° to about 60°.

21. The endovascular prosthesis defined in claim 14, wherein the rib distal portion is configured to form a rib distal portion angle with respect to a rib intermediate portion of the endovascular prosthesis.

22. The endovascular prosthesis defined in claim 21, wherein the rib distal portion angle is in the range of from about 3° to about 60°.

23. The endovascular prosthesis defined in claim 14, wherein the rib intermediate portion is configured to form a rib intermediate portion acute angle with respect to a central axis of the endovascular prosthesis.

24. The endovascular prosthesis defined in claim 23, wherein the rib intermediate portion acute angle is in the range of from about 22° to about 86°.

25. The endovascular prosthesis defined in claim 14, wherein the rib intermediate portion comprises: (i) a rib intermediate first portion connected to the rib proximal portion and configured to form a rib intermediate first portion acute angle with respect to the central axis of the endovascular prosthesis, and (ii) a rib intermediate second portion connected to the rib distal portion and configured to form a rib intermediate second portion acute angle with respect to a central axis of the endovascular prosthesis.

26. The endovascular prosthesis defined in claim 14, wherein, in two dimensions, the rib distal portion of each rib portion is directed toward the first expandable portion.

27. The endovascular prosthesis defined in claim 1, wherein the retractable leaf portion has an outer surface area comprising (i) outer surface areas of the single spine portion and the plurality of rib portions, and (ii) spaces between the outer surface areas of the single spine portion and the plurality of rib portions, and wherein, in two dimensions, the single spine portion and the plurality of rib portions attached to the single spine portion combine to occupy from about 15% to about 40% of said outer surface area of the retractable leaf portion.

28. The endovascular prosthesis defined in claim 1, wherein the single spine portion is curved about an axis substantially orthogonal to the central axis of the endovascular prosthesis.

29. The endovascular prosthesis defined in claim 28, wherein the single spine portion comprises a first radius of curvature over the length of the single spine portion about an axis transverse to the central axis of the endovascular prosthesis the first radius of curvature is variable from a proximal portion of the at least one spine portion to a distal portion of the at least one spine portion.

30. The endovascular prosthesis defined in claim 1, wherein the retractable leaf portion comprises a second radius of curvature over the length of the at least one spine portion about the central axis of the endovascular prosthesis.

31. The endovascular prosthesis defined in claim 30, wherein the second radius of curvature is variable from a proximal portion of the retractable leaf portion to a distal portion of the retractable leaf portion.

32. The endovascular prosthesis defined in claim 1, wherein the single spine portion is connected to the first expandable portion and a loop portion is connected to a distal portion of the single spine portion.

33. The endovascular prosthesis defined in claim 1, further comprising a second expandable portion expandable from a first, unexpanded state to a second, expanded state to urge the first expandable portion against a vascular lumen.

34. A method for delivering the endovascular prosthesis defined in claim 1 to a bifurcated artery having an aneurysm located at a junction of a main passageway, a first passageway and a second passageway, the method comprising the steps of:
(a) placing a guidewire and delivery catheter in the first passageway such that the guidewire emanates from the delivery catheter;
(b) passing a combination of the endovascular prosthesis interconnected to a delivery device through the delivery catheter such that the expandable portion of the endovascular prosthesis is urged against a portion of the first passageway;
(c) withdrawing the guidewire from the first passageway;
(d) placing the guidewire in the second passageway;
(e) passing the combination over the guidewire such that the leaf portion of the endovascular prosthesis is disposed across an opening of the aneurysm;
(f) detaching the delivery device from the endovascular prosthesis; and
(g) withdrawing the delivery device and the guidewire.

* * * * *